US007741288B2

(12) United States Patent
Garcia et al.

(10) Patent No.: US 7,741,288 B2
(45) Date of Patent: Jun. 22, 2010

(54) METHODS OF SCREENING OF PP1-INTERACTING POLYPEPTIDES OR PROTEINS, PEPTIDES INHIBITING PP1C BINDING TO BCL-2 PROTEINS, BCL-$X_L$ AND BCL-W, AND USES THEREOF

(75) Inventors: Alphonse Garcia, Paris (FR); Xavier Cayla, Rochecorbon (FR); Angelita Rebollo, Paris (FR)

(73) Assignees: Institut Pasteur, Paris (FR); Institut National de la Sante et de la Recherche Medicale, Paris (FR); Universite Pierre et Marie Curie (Paris 6), Paris (FR); Institut National de la Recherche Agronomique (INRA), Paris (FR)

( * ) Notice: Subject to any disclaimer, the term of this patent is extended or adjusted under 35 U.S.C. 154(b) by 0 days.

(21) Appl. No.: 10/982,891

(22) Filed: Nov. 8, 2004

(65) Prior Publication Data

US 2005/0244844 A1 Nov. 3, 2005

Related U.S. Application Data

(63) Continuation of application No. PCT/EP03/05453, filed on May 6, 2003.

(30) Foreign Application Priority Data

May 7, 2002 (EP) .................................. 02291170

(51) Int. Cl.
*A61K 38/07* (2006.01)
*A61K 38/08* (2006.01)
*A61K 38/10* (2006.01)
*C07K 5/11* (2006.01)
*C07K 7/06* (2006.01)
*C07K 7/08* (2006.01)
*G01N 33/68* (2006.01)

(52) U.S. Cl. .............................. 514/14; 436/86; 514/15; 514/17; 514/18; 530/327; 530/329; 530/330

(58) Field of Classification Search ....................... None
See application file for complete search history.

(56) References Cited

U.S. PATENT DOCUMENTS 6,884,600 B1 * 4/2005 Cohen et al. ................... 435/21

(Continued)

FOREIGN PATENT DOCUMENTS

WO WO 01/12807 * 2/2001

OTHER PUBLICATIONS

Reed, "Bcl-2 family proteins," Oncogene, 1998, 17, 3225-36.*

(Continued)

*Primary Examiner*—Jeffrey E Russel
(74) *Attorney, Agent, or Firm*—Oblon, Spivak, McClelland, Maier & Neustadt, L.L.P.

(57) ABSTRACT

The present invention relates to methods for identifying novel PP1-interacting polypeptides and proteins, compounds which are able to inhibit the binding of PP1c to certain factors naturally interacting with it, especially proteins of the Bcl-2 family (such as BCl-$x_L$ and Bcl-w), and pharmaceutical compositions comprising the same.

12 Claims, 13 Drawing Sheets

U.S. PATENT DOCUMENTS

| | | | |
|---|---|---|---|
| 7,253,269 B1* | 8/2007 | Ohta et al. ............... | 536/23.1 |
| 2003/0130484 A1* | 7/2003 | Gordon et al. ............ | 530/350 |
| 2003/0176671 A1* | 9/2003 | Reed et al. ............... | 536/23.1 |

OTHER PUBLICATIONS

Bollen, "Combinatorial control of protein phosphatase-1," TIBS, 2001, 26, 426-31.*

Ammosova et al., "Nuclear targeting of protein phosphatase-1 by HIV-1 Tat protein," J. Biol. Chem., 2005, 280, 36364-71.*

Richter et al., "Inhibitors of HIV-1 Tat-mediated transactivation," Curr. Med. Chem., 2006, 13, 1305-15, abstract only.*

Ginalski et al. "Practical lessons from protein structure prediction." Nuc. Ac. Res., 2005, 33, 1874-1891.*

Rudinger "Characteristic of the amino acids as components of a peptide hormone sequence." (Peptide Hormones (Ed. J.A. Parson). University Park Press. Baltimore, 1976, pp. 1-7.*

Pitt et al. "Single amino acid substitution mutants of *Klebsiella pneumoniae* singma54 defective in transcription" Nuc. Ac. Res., 2000, 28, 4419-4427.*

Bradley et al. "Limits of Cooperativity in a Structurally Modular Protein: Response of the Notch Ankyrin Domain to Analogous Alanine Subsitutions in Each Repeat" J. Mol. Biol., 2002, 324, 373-386.*

Flanagan et al. "Truncated staphyloccal nuclease is compact but disordered" Proc. Natl. Acad. Sci. USA, 1992, 89, 748-752.*

Schnog et al. "Sickle cell disease; a general overview" J. Med., 2004, 62, 364-374.*

Sawai et al. "Impact of single-residue mutations on the structure and function of ovispirin/novispirin antimicrobial peptides" Prot. Engin., 2002, 15, 225-232.*

Chene, "Drugs targeting protein-protein interactions," Chem. Med. Chem., 2006, 4, 400-11, abstract only.*

CAPLUS Accession No. 1995:55584.*

Oh et al. "Structure-activity relationship study: short antimicrobial peptides," J. Pept. Res., 1999, 53, 41-6.*

Lowe et al. "Structure-Function Relationships for Inhibitors of beta-Amyloid Toxicity Containing the Recognition Sequence KLVFF," Biochemistry., 2001, 40, 7882-9.*

Valerio et al. Multiple peptide synthesis on acid-labile handle derivatized polyethylene supports. International Journal of Peptide & Protein Research. 1994, vol. 44, pp. 158-165.*

Veronica Ayllon, et al., "Protein phosphatase $1\alpha$ is a Ras-activated Bad phosphatase that regulates interleukin-2 deprivation-induced apoptosis", The EMBO Journal, vol. 19, No. 10, 2000, pp. 2237-2246.

Patricia T. W. Cohen, "Protein phosphatase 1-targeted in many directions", Journal of Cell Science, vol. 115, No. 2, 2002, pp. 241-256.

Marie-Pierre Egloff, et al., "Structural basis for the recognition of regulatory subunits by the catalytic subunit protein phosphatase 1", The EMBO Journal vol. 16, No. 8, 1997, pp. 1876-1887.

Ayllon et al, J. of Immunology, 2001, vol. 166, No. 12, pp. 7345-7342.

Fernandez et al, Biochemistry 1994, vol. 33, No. 37, pp. 11073-11078.

Fukuda et al, Cancer Research 2000, vol. 60, pp. 450-456.

Ayllon et al, Eur. J. Immunol. 2002, vol. 32, No. 7, pp. 1847-1855.

* cited by examiner

FIGURE 1C
|  | IP |  |
|---|---|---|
|  | I | Bad | PP1α |
WB
Bcl-2 
Bcl-x$_L$ 
Bad 
PP1α 

FIGURE 5A

```
              101         106
         BCL-2  F S R R Y R
              181         186
                F T A R G R 97          102
         BCL-XL F E L R Y R 33          38
         BCL-w  F E T R F R
```

FIGURE 5B  *BCL-XL spots*

1  2  3  4  5  6  7  8  9  10  11

```
       136                    147
1.-   N  W  G  R  I  V  A  F  S  F  G
2.-   N  W  G  R  I  A  A  F  S  F  G 94                    105
3.-   G  D  E  F  E  L  R  Y  R  R  A  F
4.-   G  D  E  G  E  L  G  Y  G  R  A  F
5.-   G  D  E  S  E  L  S  Y  S  R  A  F
6.-   G  D  E  F  E  L  G  Y  G  R  A  F
7.-   G  D  E  F  E  L  S  Y  S  R  A  F
8.-   G  D  E  G  E  L  R  Y  R  R  A  F
9.-   G  D  E  S  E  L  R  Y  R  R  A  F
10.-  G  D  E  G  E  L  G  Y  R  R  A  F
11.-  G  D  E  S  E  L  S  Y  R  R  A  F
```

*BCL-w spots*

1  2  3  4  5  6  7  8

```
       91                   103
1.-   P  N  W  G  R  L  V  A  F  F  V  F  G
2.-   P  N  W  G  R  L  A  A  F  V  F  G 50                        62
3.-   G  D  E  F  E  T  R  F  R  R  T  F  S
4.-   G  D  E  G  E  T  G  F  G  R  T  F  S
5.-   G  D  E  F  E  T  G  F  G  R  T  F  S
6.-   G  D  E  F  E  T  R  F  G  R  T  F  S
7.-   G  D  E  G  E  T  G  F  R  R  T  F  S
8.-   G  D  E  G  E  T  R  F  R  R  T  F  S
```

FIGURE 7A
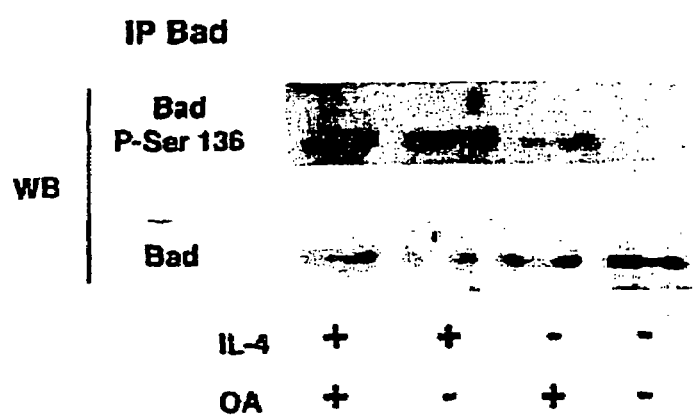
FIGURE 7B
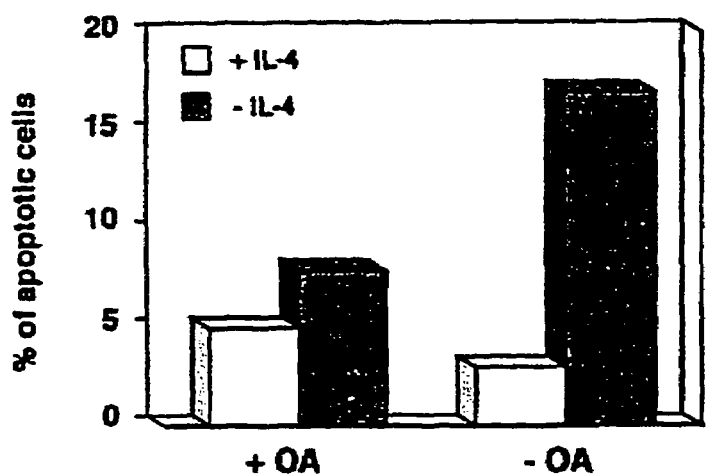
FIGURE 7C
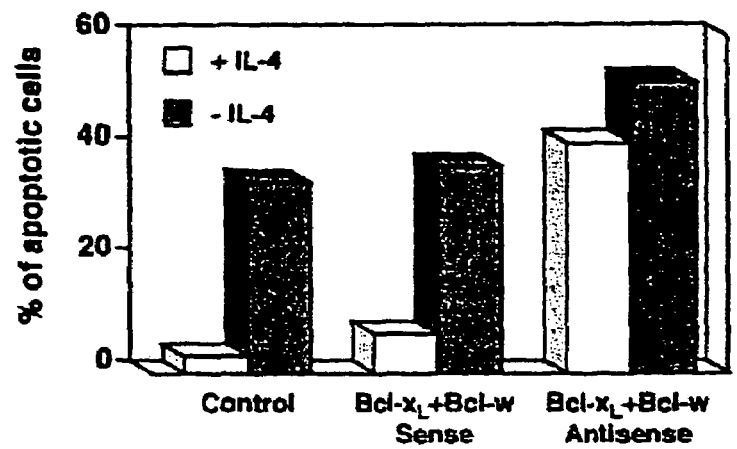
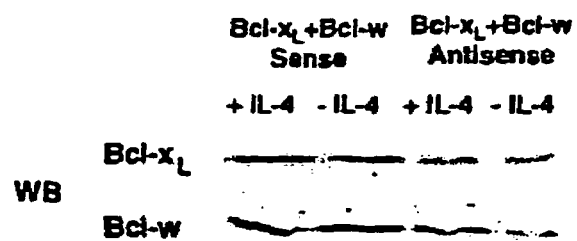

FIG. 8A

| Protein | BH3 Domain | BH1 Domain | Ref. |
|---------|------------|------------|------|
| Bcl-xL | VKQALREAGD FELRYR RAFSDTS | ELFRDGVNWG RIVAF FSFGGAL | 7 |
| Bcl-w | RAAGDE FETRRR TFSDLAAQLHV | ELFQGGPNWG RLVAF FVGA | 7 |
| Bcl-2 | HTLRQAGDD FSRRYR RDFAEMSSQ | ELFRDGVNWG RIVAF FEFGG | 6 |
| | 136 | | |
| Bad | FRGRSR S APPNLWAAQRYGRELRRMSDEEF | | |
| PP1 Binding motif | FRGRSR | | |
| | 136 | | |
| 14-3-3 Binding motif | RSRS S AP | | |

FIG. 8B

| Protein | Sequences | PP1 binding assay | |
|---------|-----------|------|---|
| Bad | 136<br>1-Wild type : E E E L S F R G R S R S A<br>2-Mutant 1 : E E E L E F R G R S R S A<br>3-Mutant 2 : E E E L G F R G R S R S A | 1<br>2<br>3 | |
| Bcl-2 | 4-Wild type : R Q A G D D F S R R Y R<br>5-Mutant 1 : R Q A G D D F E R R Y R<br>6-Mutant 2 : R Q A G D D F G R R Y R | 4<br>5<br>6 | |

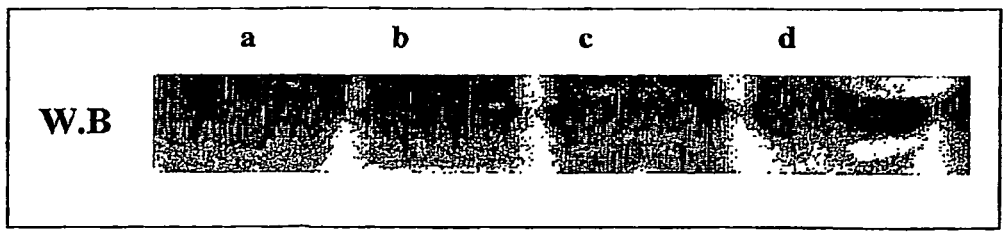

FIG. 8C

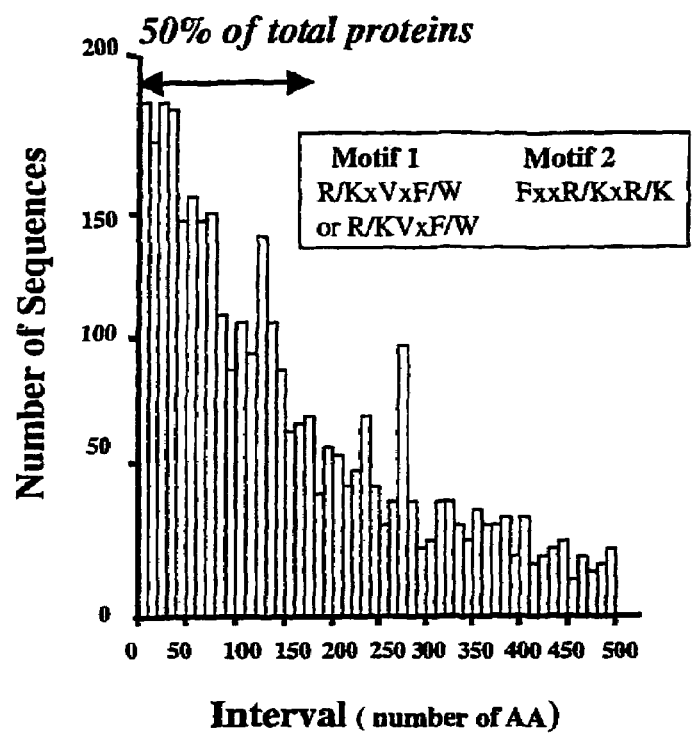
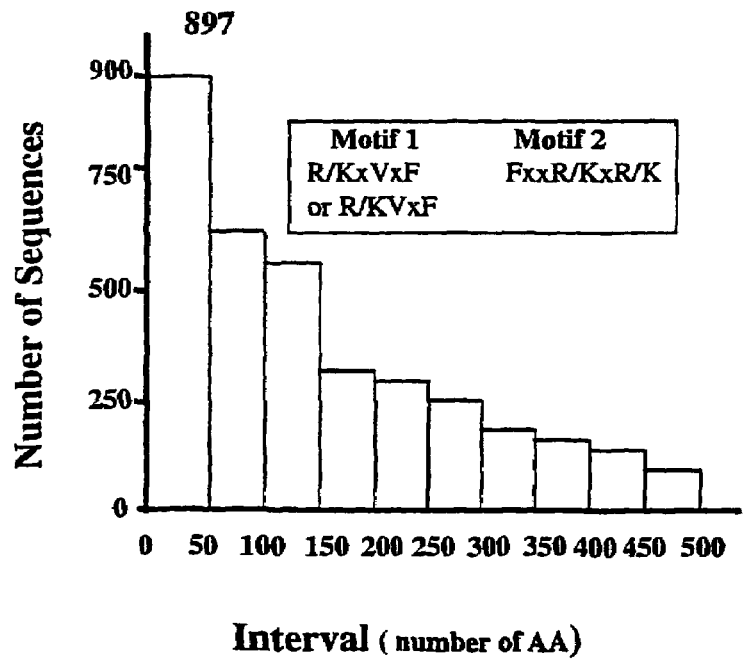
Figure 9

METHODS OF SCREENING OF PP1-INTERACTING POLYPEPTIDES OR PROTEINS, PEPTIDES INHIBITING PP1C BINDING TO BCL-2 PROTEINS, BCL-X$_L$ AND BCL-W, AND USES THEREOF

The present application is a continuation of International Application PCT/EP03/05453, filed on May 6, 2003, which claims priority to European Patent Application No. EP 02291170.5, filed on May 7, 2002.

BACKGROUND OF THE INVENTION

The invention relates to methods for identifying novel PP1-interacting polypeptides and proteins, compounds which are able to inhibit the binding of PP1c to certain factors naturally interacting with it, especially proteins of the Bcl-2 family (such as Bcl-x$_L$ and Bcl-w), and pharmaceutical compositions comprising the same.

PRIOR ART

The serine/threonine phosphatases are classified as type 1 (PP1) or type 2 (PP2), depending on their substrate specificity and sensitivity to inhibitors. PP1 regulates cell cycle progression, proliferation, transcription, protein synthesis, cytokinesis and neuronal signaling (Mc Avoy et al, 2001). PP1 is regulated by its interaction with a variety of protein subunits that target the catalytic subunit (PP1c) to specific subcellular compartments and determines its localization, activity and substrate selectivity (Bollen et al, 2001). PP1 can be regulated by the interaction between a catalytic subunit and multiple targeting subunits that allow specific dephosphorylation of diverse cellular targets. The number of known PP1c targeting subunits is continuously increasing and to date nearly thirty unique mammalian proteins have been already identified. PP1 interacting protein include the glycogen-binding subunits, RGL/GM, GL, PTG/R5/U5, and R6 which target the phosphatase to glycogen, the myosin-associating subunits, M110, NIPP-1, p99/PNUTS, and Sds22, which may direct the phosphatase to the nucleus (Bollen, 2001). Previous studies based on structural and X-ray crystallography analysis of PP1 interacting proteins indicated that PP1c binds to distinct known interacting proteins through a short amino-acid sequence. The [RK]VxF (or [RK]xVxF) motifs represent a widespread consensus sequence for the recognition and binding of distinct regulatory subunits and interacting proteins with PP1c (Egloff et al, 1997; Aggen et al, 2000).

Using a murine T cell line that can be propagated independently in the presence of IL-2 or IL-4 (Pitton et al, 1993), the inventors have described that PP1c is a Ras-activated phosphatase that dephosphorylates Bad (a pro-apoptotic member of the Bcl-2 protein family) prior to induce apoptosis in response to IL-2 deprivation (Ayllón et al, 2000). By performing biochemical competitive studies, the inventors also recently identified Bcl-2 as a new targeting subunit of PP1c that controls its association to Bad in IL-2-stimulated cells (Ayllón et al, 2001).

The Bcl-2 family proteins act as an intracellular checkpoint in the apoptotic pathway. The Bcl-2 family of proteins is divided into two functional groups: anti-apoptotic members such as Bcl-2, Bcl-x$_L$, Bcl-w, A1 and Mcl-1 and pro-apoptotic members such as Bax, Bak, Bcl-x$_S$ as well as the BH3-only member Bad (White, 1996; Reed, 1998; Chao and Korsmeyer, 1998). Balance between homo- and hetero-dimers of Bcl-2 family members may be critical to maintain cell proliferation or apoptosis (Jacobson, 1997; Korsmeyer, 1999; Gross et al, 1999). Up- or down-regulation of these proteins may account for survival of some cell types, although it is also possible that survival factors use protein kinases or phosphatases to alter the ability of these proteins to promote cell survival or apoptosis. Anti-apoptotic Bcl-2 family members interact with other death agonists of the Bcl-2 family and with non-Bcl-2 family proteins, including R-Ras, H-Ras, Raf, caspases, calcineurin and the serine/threonine phosphatase PP1c (Rebollo et al, 1999; Ayllón et al, 2001). The Bcl-2 family has been defined by sequence homology based upon specific conserved motifs termed Bcl-homology regions (BH1, BH2, BH3 and BH4 domains). BH1, BH2 and BH3 domains have been shown to be important in homodimerization or heterodimerization and in modulating apoptosis. Anti-apoptotic molecules have a specific BH4 domain.

Bad shares identity only in the BH3 domain (Zha et al, 1997) and forms hetero-dimers with Bcl-2 and Bcl-x (Ottilie et al, 1997). Upon stimulation of cells with IL-3, NGF and GM-CSF, Bad becomes serine phosphorylated (Del Peso et al, 1997; Datta et al, 1997), resulting in association-to the 14-3-3 protein and abolishing interaction with Bcl-x (Hsu et al, 1997). It has been recently shown that association of 14-3-3 protein to Bad is dependent on serine 155 phosphorylation of Bad (Datta et al, 2000; Zhou et al, 2000).

Bcl-w is a pro-survival protein bearing the four conserved Bcl-2 homology (BH) domains (Gibson et al, 1996). Enforced expression of Bcl-w, like Bcl-2, renders lymphoid and myeloid cell lines resistant to apoptosis induced by cytokine deprivation. The anti-apoptotic molecule Bcl-x$_L$ also contains the four BH conserved domains (Núñez et al, 1994). A second Bcl-x isoform, Bcl-x$_S$, encodes a smaller protein of 170 amino acids that enhances apoptosis (Minn et al, 1996). Bcl-x$_L$ contains a hydrophobic segment at the C-terminal end that is believed to serve as a membrane anchor (Boise et al, 1993).

Apoptosis or programmed cell death is an active process in which cells induce their self-destruction in response to specific cell death signals or in the absence of cell survival signals. This active process is actually essential in the normal development and homeostasis of multicellular organisms. It is opposed to necrosis which is cell death occurring as a result of severe injurious changes in the environment.

Various pathologies occur due to a defective or aberrant regulation of apoptosis in the affected cells of an organism. For example, defects that result in a decreased level of apoptosis in a tissue as compared to the normal level required to maintain the steady-state of the tissue can promote an abnormal increase of the amount of cells in a tissue. This has been observed in various cancers, where the formation of tumors occurs because the cells are not dying at their normal rate. Some DNA viruses such as Epstein-Barr virus, African swine fever virus and adenovirus, also inhibit or modulate apoptosis, thereby repressing cell death and allowing the host cell to continue reproducing the virus.

To the contrary, a defect resulting in an increase of cell death in a tissue may be associated with degenerative disorders wherein cells are dying at a higher rate than they regenerate. This is observed in various disorders, such as AIDS, senescence, and neurodegenerative diseases.

Compounds that modulate positively or negatively apoptosis can provide means for the treatment or the prevention of these disorders. As a consequence, the delineation of apoptotic pathways provides targets for the development of therapeutic agents that can be used to modulate the response of a cell to apoptotic or cell survival signals.

The results disclosed in the present invention indicate that the anti-apoptotic members of the Bcl-2 family, Bcl-w and Bcl-$x_L$ are also targeting subunits of PP1c in IL-4-stimulated cells. This observation offers a way to a novel general mechanism of regulation of cell apoptosis that may play a role in the regulation of pro- or anti-apoptotic molecules in response to cell death or cell survival signals. The invention is therefore of a particular importance in the fields of cancer therapy and neurodegenerative diseases therapy.

More generally, the present invention provides means to modulate the interaction between PP1 and the proteins or polypeptides that bind to it Therefore, the present invention has applications in a wide range of fields, since PP1 is involved in many biological pathways. For example, it is known that a decrease in phosphorylation of the PP1 complex activates the smooth muscle myosin light chains and hence relaxes smooth muscles (see, Uehata et al., 1997). High blood pressure could hence be a target of the present invention.

PP1 is a major eukaryotic protein serine/threonine phosphatase that regulates diverse cellular processes such as cell cycle, transcription and protein synthesis.

PP1-regulation can also effect the downstream regulation of hepatic glycogen synthesis which in turn would lower blood glucose levels and thus treat diabetes in which hyperglycemia is a severe problem.

Moreover, PP1 is involved in several bacterial, viral and parasitic infections, and inhibiting its interaction with some of its partners in an infectious context could be beneficial to the patient.

SUMMARY OF THE INVENTION

To be concise, the following Summary, the Preferred Embodiments and the Examples of the present invention are described below, it being understood that literal word-for-word description of all of the embodiments and combinations thereof would be recognized by the person skilled in the art and hence, literally repetiveness not being necessary. It should be appreciated that the Examples, as well as the preferred embodiments, the Summary of the Invention and certain aspects of the prior art, can be combined in all variations; one aspect of the invention combined with another irregardless of their place in this description of the entire specification, without deviating from the present invention, as recognized by the person skilled in the art, without any limitations.

Thus, the present invention relates to a peptide or a set of peptides which mimicks both the motifs M1 and M2 and which is able to inhibit the Bcl-$x_L$/PP1c, the Bcl-w/PP1c, or the Bcl-2/Bad/PP1c interactions, wherein the motif M1 has the sequence FXX[RK]X[RK], and the motif M2 has the sequence [RK]VX[FW] or [RK]XVX[FW], wherein X is any amino acid.

In another embodiment, the present invention relates to a set of peptides comprising R (NWGRIVAFFSF) (SEQ ID NO: 6) and F (GDEFELRYRRAF) (SEQ ID NO: 7) peptides.

In yet another embodiment the present invention relates to a pharmaceutical composition comprising a peptide or a set of peptides which mimicks both the motifs M1 and M2 and which is able to inhibit the Bcl-$x_L$/PP1c, the Bcl-w/PP1c, or the Bcl-2/Bad/PP1c interactions. Such a composition can, for example, comprise R (NWGRIVAFFSF) (SEQ ID NO: 6) and F (GDEFELRYRRAF) (SEQ ID NO: 7) peptides. Peptides with modified amino acids (glycosylation, acetylation, phosphorylation, amidation or derivation by known protecting/blocking groups) can also be used in the compositions according to the invention.

In yet another embodiment the present invention relates to a pharmaceutical composition comprising a vector comprising a nucleic acid encoding a peptide or a set of peptides which mimicks both the motifs M1 and M2.

In another embodiment the present invention relates to a method of identifying a PP1-interacting polypeptide or protein, comprising detecting in the sequence of a polypeptide or protein, the presence of two PP1-binding motifs M1 and M2.

In yet another embodiment the present invention discloses a method of screening compounds that interact with PP1 regulators, wherein peptides which mimick both the motifs M1 and M2 and which are able to inhibit the Bcl-$x_L$/PP1c, the Bcl-w/PP1c, or the Bcl-2/Bad/PP1c interactions, are immobilized on a support and the interaction of said compounds with said peptides are tested.

In yet another embodiment, the present invention relates to a method of screening compounds that interact with PP1. This method comprises obtaining antibodies to peptides which mimick both the motifs M1 and M2 and which are able to inhibit the Bcl-$x_L$/PP1c, the Bcl-w/PP1c, or the Bcl-2/Bad/PP1c interactions, and testing the interaction of said compound with said antibodies.

In another embodiment, the present invention relates to a method for inhibiting in vitro the interaction between PP1c and Bcl-$x_L$ or Bcl-w, comprising a step of adding a peptide or a set of peptides which mimicks both M1 and M2.

In the above methods, the peptides which mimic both the motifs M1 and M2 and which are able to inhibit the Bcl-$x_L$/PP1c, the Bcl-w/PP1c, or the Bcl-2/Bad/PP1c interaction can be for example the R (NWGRIVAFFSF) (SEQ ID NO: 6) and F (GDEFELRYRRAF) (SEQ ID NO: 7) peptides.

In yet another embodiment, the present invention relates to a kit comprising peptides which mimic both the motifs M1 and M2 and which are able to inhibit the Bcl-$x_L$/PP1c, the Bcl-w/PP1c, or the Bcl-2/Bad/PP1c interactions. Such a kit can, for example, comprise R (NWGRIVAIFFSF) (SEQ ID NO: 6) and F (GDEFELRYRRAF) (SEQ ID NO: 7) peptides. These peptides may be immobilized on a solid support.

In yet another embodiment the present invention relates to a kit containing antibodies to peptides which mimick both the motifs M1 and M2 and which are able to inhibit the Bcl-$x_L$/PP1c, the Bcl-w/PP1c, or the Bcl-2/Bad/PP1c interactions. Said antibodies can for example be raised against R (NWGRIVAFFSF) (SEQ ID NO: 6) and F (GDEFELRYRRAF) (SEQ ID NO: 7) peptides.

In yet another aspect, the present invention relates to a method for treating animals and vegetables that have any disease involved in the PP1c pathway, comprising administering to animals and vegetables in need of such treatment peptides which mimick both the motifs M1 and M2 and which are able to inhibit the Bcl-$x_L$/PP1c, the Bcl-w/PP1c, or the Bcl-2/Bad/PP1c interactions.

In yet another aspect, the present invention relates to a method for treating an animal that has diabetes or hypertension or a neurological disorder or a viral infection or a parasitic infection, comprising administering to an animal in need of such treatment peptides which mimick both the motifs M1 and M2 and which are able to inhibit the Bcl-$x_L$/PP1c, the Bcl-w/PP1c, or the Bcl-2/Bad/PP1c interactions.

In the above methods, R (NWGRIVAFFSF) (SEQ ID NO: 6) and F (GDEFELRYRRAF) (SEQ ID NO: 7) peptides can for example be administered.

In another embodiment, the present invention relates to the use of peptides which mimick both the motifs M1 and M2 and which are able to inhibit the Bcl-$x_L$/PP1c, the Bcl-w/PP1c, or the Bcl-2/Bad/PP1c interactions, to treat diabetes or hypertension or neurological disorders or a viral infection or a parasitic infection.

In yet another embodiment the present invention relates to the use of peptides which mimic both the motifs M1 and M2 and which are able to inhibit the Bcl-$x_L$/PP1c, the Bcl-w/PP1c, or the Bcl-2/Bad/PP1c interactions, for the preparation of a medicament to treat diabetes or hypertension or neurological disorders or a viral infection or a parasitic disease. R (NWGRIVAFFSF) (SEQ ID NO: 6) and F (GDEFELRYR-RAF) (SEQ ID NO: 7) peptides can for example be used according to the invention.

A) Cytoplasmic extracts from IL-4-stimulated (60 U/ml) or -deprived cells were immunoprecipitated with anti-Bcl-$x_L$ or anti-Bcl-w antibody, transferred to nitrocellulose and blotted with anti-Bad, anti-PP1c, anti-Bcl-$x_L$ and anti-Bcl-w antibody. Protein bands were detected using ECL system. Molecular weights of the corresponding proteins is shown. Similar results were obtained in three independent experiments. B) Cytoplasmic extracts from IL-4-stimulated cells were immunoprecipitated with anti-p55 IL-2R chain antibody, transferred to nitrocellulose and blotted with anti-Bcl-w, Bcl-$x_L$ or anti-p55 IL-2R antibodies. Protein bands were detected using the ECL system. C) Cytoplasmic extracts from freshly isolated thymocytes were immunoprecipitated with anti-Bad, anti-PP1c or an irrelevant serum and blotted with anti-Bcl-2, anti-Bcl-$x_L$, anti-Bad and anti-PP1c. Proteins were detected as in A. Similar results were obtained in three independent experiments.

FIG. 2. Effect of IL-4-deprivation on Bad, PP1c, Bcl-$x_L$ and Bcl-w expression.

A) Ts1αβ cells were IL-4-stimulated or -deprived for the times indicated, then lysed. Proteins were transferred to nitrocellulose and probed with anti-Bcl-$x_L$, anti-Bcl-w, anti-Bad and anti-PP1c antibodies. Similar results were obtained in two independent experiments.

B) Cytoplasmic extracts from IL-4-stimulated or 24 h-deprived cells were immunoprecipitated with anti-Bcl-$x_L$ or anti-Bcl-w, separated in a gradient SDS-PAGE gel and blotted with anti-Pser, anti-Bad, anti-PP1c and, as internal control, with anti-Bcl-$x_L$ and Anti-Bcl-w. Similar results were obtained in three independent experiments.

C) Cytoplasmic extracts from control, IL-4 stimulated or deprived cells (1×10$^7$) were immunoprecipitated with anti-Bad antibody and blotted with anti-Bad serine 112, serine 136 and serine 155. As internal control, the blot was developed with anti-Bad antibody. Similar results were obtained in two independent experiments. Positive control for serine 112 and 136 phosphorylation of Bad, IL-2 stimulated cells (lane C); positive control for serine 155 phosphorylation of Bad, Bad-transfected COS cells (lane C).

D) Total extracts (T) of cytoplasmic lysates from IL-4-stimulated or deprived cells (1×10$^7$) were immunoprecipitated with anti-PP1c, anti-Raf, anti-Bcl-$x_L$ or anti-Bad antibody and blotted with anti-14-3-3, anti-PP1c, anti-Bcl-$x_L$ and anti-Bad. Similar results were obtained in two independent experiments.

Figure 3A:
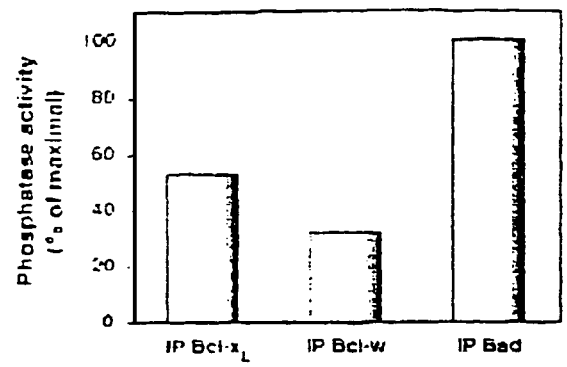
Figure 3B:
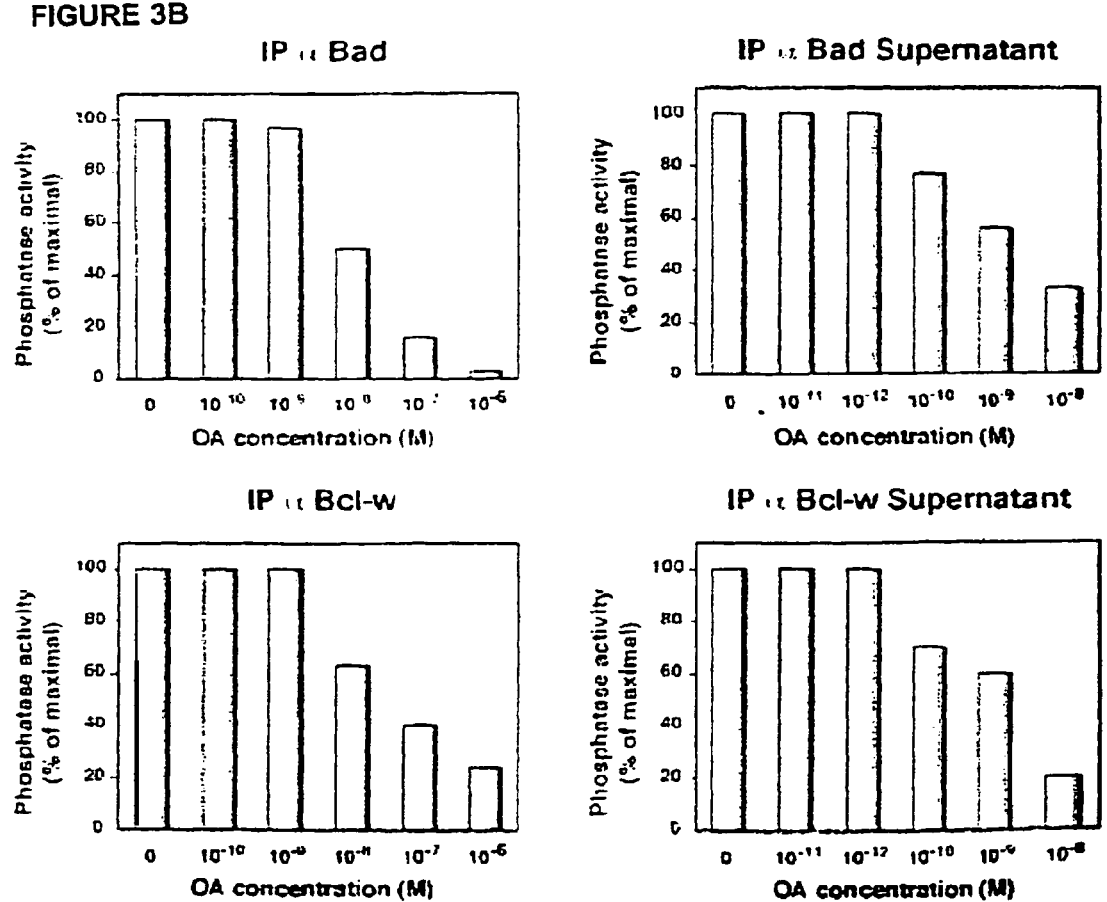

FIG. 3. Estimation of serine/threonine phosphatase activity in control or OA-treated Bcl-x, Bad and Bcl-w immunoprecipitates.

A) Phosphatase activity was estimated in Bad, Bcl-$x_L$ and Bcl-w immunoprecipitates from IL-4-stimulated cells using $^{32}$P phosphorylase a as substrate.

B) Different concentrations of OA were added to Bad or Bcl-w immunoprecipitates from IL-4 stimulated cells. Phosphatase activity was estimated using $^{32}$P phosphorylase a as substrate. The reaction was as in A. Similar results were obtained in three independent experiments. Phosphatase activity is represented as the percentage of maximal activity in untreated supernatants.

FIG. 4. Estimation of serine/threonine phosphatase activity after Bcl-$x_L$ and Bcl-w depletion.

A) Bcl-$x_L$ and Bcl-w were depleted from cytoplasmic lysates of IL-4 stimulated cells by four sequential immunoprecipitations. Phosphatase activity was estimated in Bad immunoprecipitates from control IL-4-stimulated cells or in Bad immunoprecipitates depleted of Bcl-$x_L$ and Bcl-w after four sequential immunoprecipitations. Phosphatase activity is represented as the percentage of the maximal activity detected in control anti-Bad immunoprecipitates. B) The effect of Bcl-$x_L$ and Bcl-w depletion in PP1c/Bad association was analyzed. Cytoplasmic extracts from control IL-4-stimulated cells or Bcl-$x_L$, and Bcl-w depleted cytoplasmic extracts were immunoprecipitated with anti-Bad or anti-PP1c antibody and blotted with anti-Bad, anti-Bcl-w, anti-Bcl-$x_L$ and anti-PP1c. Similar results were obtained in three independent experiments. Protein bands were detected using the ECL system.

FIG. 5. PP1c binding assay on cellulose-bound Bcl-$x_L$ or Bcl-w peptides.

A) Sequence of F X X R X R motif of Bcl-2, Bcl-$x_L$ and Bcl-w. B) Membrane with Bcl-$x_L$ or Bcl-w peptides containing the R/K X V/I X F or F X X R X R motif, as well as peptides containing mutated motifs were incubated with purified PP1c, followed by anti-PP1c antibody and PO-conjugated secondary antibody. Spots were detected using ECL system. The R/K X V/I X F and F X X R X R motifs are in bold. Mutated amino acids into the motif are in bold and underlined. Similar results were obtained in two independent experiments. Peptide 1 corresponds to the PP1 binding motif of Bcl-$x_L$ and Bcl-w. Peptide 2 corresponds to the mutated PP1 binding site were V and F residues were mutated to A. FIG. 5b contains the following sequences: NWGRIVAFF-SFG (SEQ ID NO: 6), NWGRIAAAFSFG (SEQ ID NO: 51): GDEFELRYRRAF (SEQ ID NO: 7). GDEGELGYGRAF (SEQ ID NO: 59): GDESELSYSRAF (SEQ ID NO: 54). GDEFELGYGRAF (SEQ ID NO: 55): GDEFELSYSRAF (SEQ ID NO: 56). GDEGELRYRRAF (SEQ ID NO: 57): GDEGELRYRRAF (SEQ ID NO: 58): GDEGELGYRRAF (SEQ ID NO: 59). GDESELSYRRAF (SEQ ID NO: 60). PNWGRLVAFFVFG (SEQ ID NO: 61): PNWGR-LAAAFVFG (SEQ ID NO: 62). GDEFETRFRRTFS (SEQ ID NO: 63): GDEFETGFGRTFS (SEQ ID NO: 64). GDE-FETGFGRTFS (SEQ ID NO: 65), GDEFETRFGRTFS (SEQ ID NO: 66). GDEGETGFRRTFS (SEQ ID NO: 67). GDE-GETRFRRTFS (SEQ ID NO: 68). FIG. 5a contains the following sequences FSRRYR (SEQ ID NO: 5). FTARGR (SEQ ID NO: 5). FELRYR (SEQ ID NO: 5). FETRFR (SEQ ID NO: 5).

Figure 6A:
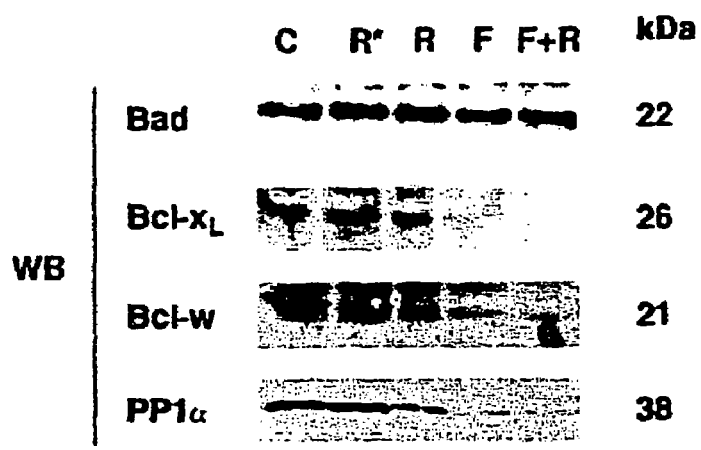
Figure 6B:
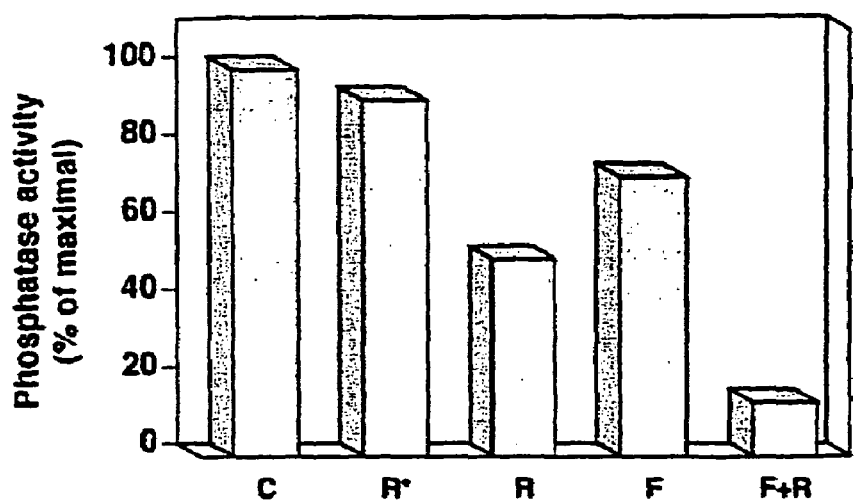
Figure 6C:
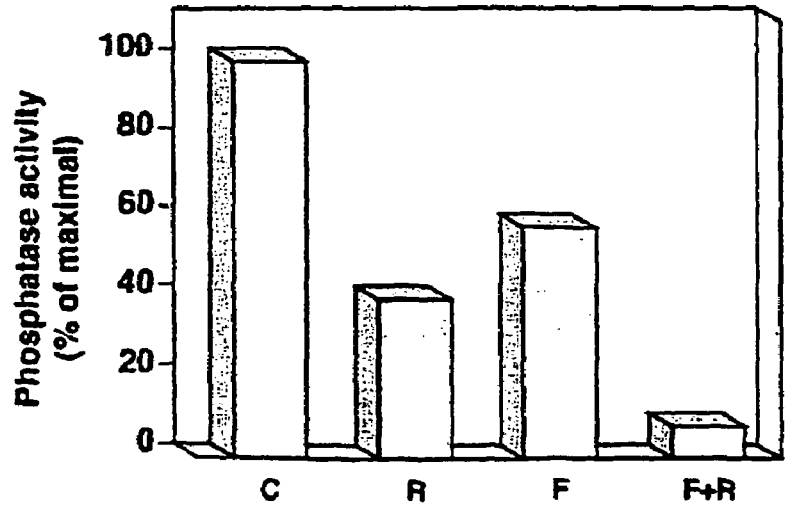

FIG. 6. Effect of R, R*, F and R+F peptides on the interaction Bcl-$x_L$/PP1c/Bad and Bcl-w/PP1c/Bad.

A) Cytoplasmic extracts from control IL-4-stimulated cells were immunoprecipitated with anti-Bad antibody. The interaction Bcl-$x_L$/PP1c/Bad and Bcl-w/PP1c/Bad was competed with 1.5 mM of R, R*, F or R+F peptides for 30 min at room temperature. Immunoprecipitates were washed, transferred to nitrocellulose and blotted with anti-Bad, anti-PP1c, anti-Bcl-$x_L$ and anti-Bcl-w. Similar results were obtained in two independent experiments. For sequence of peptides, see Materials and Methods or FIGS. 5A and 5B.

B) Cytoplasmic lysates from IL-4-stimulated cells were immunoprecipitated with anti-Bad antibody. Immunoprecipitates were treated with 1.5 mM of R, R*, F or R+F peptides for 30 min at room temperature. Immunoprecipitates were washed and phosphatase activity estimated using $^{32}$P phosphorylase a as substrate. Similar results were obtained in two independent experiments.

C) Cytoplasmic lysates from IL-4-stimulated cells were immunoprecipitated with anti-Bad antibody and then treated with 1.5 mM of R+F peptide or 3 mM of R or F peptide (30 min, room temperature). Immunoprecipitates were washed and phosphatase activity estimated as in B.

FIG. 7. Effect of OA and antisense oligonucleotides on apoptosis and serine 136 phosphorylation of Bad.

A) Cells were treated with or without 1 µM OA in the presence or the absence of IL-4. Cytoplasmic lysates were immunoprecipitated with anti-Bad antibody, transferred to nitrocellulose and probed with phospho-Bad ser 136 and anti-Bad, the latter to verify that OA treatment in vivo does not affect Bad expression. Protein bands were detected using ECL.

B) Cells were treated for 6 h with or without 1 µM OA in the presence or absence of IL-4 and then washed, stained with propidium iodide and analyzed by flow cytometry.

C) Cells were treated for 24 h with or without 15 µM sense or antisense oligonucleotide in the presence or the absence of IL-4. Oligonucleotides were added a 0, 12 and 18 h and then cells were washed, stained with propidium iodide and analyzed by flow cytometry. The expression of Bcl-$x_L$ and Bcl-w upon sense and antisense treatment was analyzed by western blot.

FIG. 8: A) Two putative PP1 binding motifs in Bcl-2 proteins Sequence alignment in the vicinity of BH1 and BH3 domain of some Bcl-2 proteins. These sequences are perfectly conserved in various species (human, mouse, rat, bovine . . . ).

FIG. 8A contains the following sequences:
VKQALREAGDFELRYRFAFSDTS (SEQ ID NO: 69)
ELFRDGVNWGRIVAFFSFGGAL (SEQ ID NO: 70)
RAAGDEFETRRRTFSDLAAQLHV (SEQ ID NO: 71)
ELFQGGPNWGRLVAFFVGA (SEQ ID NO: 72)
HTLRQAGDDFSRRYRRDFAEMSSQ (SEQ ID NO: 73)
ELFRDGVNWGRIVAFFEFGG (SEQ ID NO: 74)
FRGRSSRSAPPNLWAAQRYGELRRMSDEEF(SEQ ID NO: 75)
FRGRSR (a fragment of SEQ ID NO: 75), and
RSRSSAP (SEQ ID NO: 84).

B) A role for Serine phosphorylation in PP1 binding

Six peptides (of 14 AA length) were synthesized and covalently linked to a cellulose membrane prior to be analyzed for PP1-binding as described. A punctual AA mutation in Ser-136 was introduce in 4 peptides (mutant2, 3,5,6).

FIG. 8B contains the sequences EEELSFRGRSRSA (SEQ ID NO: 78), EEELEFRGRSTSA (SEQ ID NO; 79), EEEL-GFRGRSRSA (SEQ ID NO: 80), RQAGDDFSRRYR (SEQ ID NO: 81), RQAGDDFERRYR (SEQ ID NO: 82) and RQAGDDFGRRYR (SEQ ID NO: 83).

C) Association of P13-K p 85 (lane 1), P13-K p110 (lane 2), HSP70, (lane 3),and CD4 (lane 4) to PP1c.

IL-4 treated TS1 αβ cells (1×10$^7$) were used for immunoprecipitation as usually described. Immunoprecipitates were transferred to nitrocellulose, blocked and incubated with anti-PP1c primary antibody. Membrane was washed and incubated with PO-conjugated secondary antibody and proteins were developed using the ECL.

FIG. 9: Histogram to illustrate the number of proteins and the number of amino-acids distancing the F-x-x-[RK]-x-[RK] and [RK]-V-x-[FW]/[RK]-x-V-x-[FW](A)[RK]-V-x-F/[RK]-x-V-x-F (B) motifs.

PREFERRED EMBODIMENTS OF THE INVENTION

The following terms that are used throughout the remaining specification and claims and should be understood to mean, besides the generic definition, the following more precise definition; it being understood that the generic definitions are also included.

As used herein, the word "aspect" means any technical feature or element of the claimed invention.

As used herein, the word "mimick" means close resemblance to either in structure and/or function.

As used herein the word "isolated" means taken from the natural environment. Isolated does not necessarily mean that what is taken from the natural environment is 100% purified.

As used herein the term "biochemical test" means any test which is capable of identifying an interacting polypeptide or protein. Examples of a biochemical tests include, but are not limited to, immunoprecipitation, use of antibodies, either monoclonal or polyclonal, oligonucleotide probes that can be labelled with radioactivity or an enzyme, GST pulldown (gel filtration experiment revealing size of macromolecular complexes) as described in Ayllón et al EMBO J. 19 2237-2246 (2000), and the like.

As used herein, the term "motif" means a particular amino acid sequence or sequences which are similar and have the same function in different cellular environments. A motif has some fixed amino acids and some variable ones.

As used herein and throughout the entire specification and in the claims, when several amino acids are bracketed, this means that the amino acid within the brackets can be one or the other. Thus [RK] means that the motif can have either R or K.

As used herein, the word "inhibits" means to prevent the specific interactions, regardless of the mechanism of this prevention.

As used herein a "pharmaceutical composition" includes, but is not limited to, the peptides of the present invention disclosed throughout the specification and a pharmaceutically acceptable carrier. This pharmaceutical composition comprises a pharmaceutically acceptable amount of the peptides of the present invention. The pharmaceutically acceptable amount can be estimated from cell culture assays. For example, a dose can be formulated in animal models to achieve a circulating concentration range that includes or encompasses a concentration point or range having the desired effect in an in vitro system. This information can thus be used to accurately determine the doses in animals, including humans.

The therapeutically effective dose refers to that amount of the compound that results in amelioration of symptoms in a patient. Toxicity and therapeutic efficacy of such compounds can be determined by standard pharmaceutical procedures in cell cultures or in experimental animals. For example, the LD50 (the dose lethal to 50% of the population) as well as the ED50 (the dose therapeutically effective in 50% of the population) can be determined using methods known in the art. The dose ratio between toxic and therapeutic effects is the therapeutic index which can be expressed as the ratio between LD 50 and ED50 compounds that exhibit high therapeutic indexes.

The data obtained from the cell culture and animal studies can be used in formulating a range of dosage of such compounds which lies preferably within a range of circulating concentrations that include the ED50 with little or no toxicity.

The pharmaceutical composition can be administered via any route such as locally, orally, systemically, intravenously, intramuscularly, mucosally, using a patch and can be encapsulated in liposomes, microparticles, microcapsules, and the like. The pharmaceutical composition can be embedded in liposomes or even encapsulated. The pharmaceutical composition can also be in a lyophilized form.

Any pharmaceutically acceptable carrier or adjuvant can be used in the pharmaceutical composition. The modulating compound will be for instance in a soluble form combined with a pharmaceutically acceptable carrier. The techniques for formulating and administering these compounds can be found in "*Remington's Pharmaceutical Sciences*" Mack Publication Co., Easton, Pa., latest edition.

The mode of administration optimum dosages and galenic forms can be determined by the criteria known in the art taken into account the seriousness of the general condition of the mammal, including the human, the tolerance of the treatment and the side effects.

"Pharmaceutical compositions" also include vectors which can be administered directly in vivo or can be combined with specific cells that can be or may not be extracted from the animal to be treated. Types of cells include all eukaryotic and prokaryotic cells including muscle, heart, liver, lung, brain cells, thymocytes, blood and the like. Plant and bacterial cells are also encompassed in the present invention since the PP1 is found in many different types of plant and bacterial cells. Yeast cells are also encompassed by the present invention. In fact any cell that contains PP1 is encompassed by the present invention.

Thus encompassed by the term "pharmaceutical compositions" are included all forms of not only classic pharmaceutical administration, but also include gene therapy.

By the term "support" is meant any type of object on which peptides can be immobilized. The type of support includes, but is not limited to, costar wells, beads, resins, glass chips, membranes and the like. Any support which can be used to immobilize proteins or peptides can be used in the methods of the present invention.

The term "animal" encompasses any living being which is not vegetal, including vertebrates such as mammals, birds, reptiles, amphibians and fish.

As used herein the terms "polynucleotides", "nucleic acids" and "oligonucleotides" are used interchangeably and include, but are not limited to RNA, DNA, RNA/DNA sequences of more than one nucleotide in either single chain or duplex form. The polynucleotide sequences of the present invention may be prepared from any known method including, but not limited to, any synthetic method, any recombinant method, any ex vivo generation method and the like, as well as combinations thereof.

Polynucleotides which can hybridize to any of the polynucleotides discussed above are also covered by the present invention. Such polynucleotides are referred to herein as "hybridizing" polynucleotides. Hybridizing polynucleotides can be useful as probes or primers, for example.

According to an embodiment of the present invention, such hybridizing molecules are at least 10 nucleotides in length. According to another embodiment, they are at least 25 or at least 50 nucleotides in length.

In an embodiment, the hybridizing molecules will hybridize to such molecules under stringent hybridization conditions. One example of stringent hybridization conditions is where attempted hybridization is carried out at a temperature of from about 35° C. to about 65° C. using a salt solution which is about 0.9 molar. However, the skilled person will be able to vary such conditions as appropriate in order to take into account variables such as probe length, base composition, type of ions present, etc.

By "preventing or treating" is meant to manage a disease or medical condition or to arrest the onset of a disease or a medical condition.

More specifically, the present invention relates to a peptide or a set of peptides which mimicks both motifs M1 and M2 and which affects the Bcl/$x_L$/PP1c, the Bcl-w/PP1c, or the Bcl-2/Bad/PP1c interactions, wherein the motif M1 has the sequence FXX[RK]X[RK], and the motif M2 has the sequence [RK]VX[FW] or [RK]XVX[FW], wherein X is any amino acid.

In a specific embodiment, the present invention relates to set of peptides comprising the R (NWGRIVAFFSF) (SEQ ID NO: 6) peptide and the F (GDEFELRYRRAF) (SEQ ID NO: 7) peptide.

The present invention does not only encompass the specific peptides or set of peptides described above, but also modified peptides in which an amino acid is deleted, added or changed while retaining the same function of inhibiting the Bcl-$x_L$/PP1c, the Bcl-w/PP1c, or the Bcl-2/Bad/PP1c interactions. In particular, chemical analogs of the amino acids can be used, such as phosphorylated or thiophosphorylated amino acids. For example, it has been demonstrated that a phosphorylated Y is similar to the F residue. Thus, these two amino acids may be interchanged without effecting the function of the motif.

Peptidic analogues of the motifs are thus encompassed in the present invention. These analogues include those structures that are similar in function but are not identical in composition. An example of an analogue is a polypeptide that has chemically modified amino acids which are phosphorylated and cannot be dephosphorylated by the cellular enzymes.

The peptides or sets of peptides according to the present invention, or included in the compositions and kits of the invention, can encompass two or more motifs on the same molecule, or 2 to 5 motifs, or 2 to 10 motifs, which motifs are described above, having a spacer between them. The spacer may be a sequence of amino acids or a hydrocarbon chain interposed by covalent linkages. A spacer can also be any chemical entity which can serve to connect the at least two motifs, and the spacer can also contain regulatory sequences between the at least two motifs.

In another embodiment, the spacer of the present invention has from about 1 to about 50 amino acids. In a particular embodiment, the spacer has about 36 amino acids.

In another embodiment, the present invention relates to a fusion polypeptide or protein containing at least one motif of the present invention. This fusion polypeptide or protein can be made according to methods known in the art such as those described in Sambrook et al, Molecular Cloning A Laboratory Manual $2^{nd}$ Edition (1989). A particular fusion polypeptide or protein of the invention comprises one or several motifs M1 or M2, linked with at least one fusogenic peptide which will help the fusion polypeptide or protein enter target cells. Said fusogenic peptide can be for example a viral epitope or a ligand to a specific cell receptor such as chemokine receptors.

The above motifs, their analogues and modifications can be synthesized using, for example, an "Applied System" synthesizer or by Merrifield type solid phase synthesis (See, Merrifield, Adv. Enzmol. Related Areas Mol. Biol. (1969) 32; 221-96 or Merrfield, Recent Prog. Horm. Res.(1967); 23; 451-82) The motifs can also be recombinantly produced.

The nucleic acid sequence encoding the motifs can be inserted into an expression vector which contains the necessary elements for the transcription and translation of the inserted peptide/protein-coding sequence. Such transcription elements include a regulatory region and a promoter. Thus, the nucleic acid which can encode a marker compound of the present invention is operably linked to a promoter in the expression vector. The expression vector can also include a replication origin.

A wide variety of host/expression vector combinations are employed in expressing the nucleic acids of the present invention. Useful expression vectors that can be used include, for example, segments of chromosomal, non-chromosomal and synthetic DNA sequences. Suitable vectors include, but are not limited to, derivatives of SV40 and pcDNA and known bacterial plasmids such as col El, pCR1, pBR322, pMal-C2, pET, pGEX as described by Smith et al (1988), pMB9 and derivatives thereof, plasmids such as RP4, phage DNAs such as the numerous derivatives of phage I such as NM989, as well as other phage DNA such as M13 and filamentous single stranded phage DNA; yeast plasmids such as the 2 micron plasmid or derivatives of the 2m plasmid, as well as centomeric and integrative yeast shuttle vectors; vectors useful in eukaryotic cells such as vectors useful in insect or mammalian cells; vectors derived from combinations of plasmids and phage DNAs, such as plasmids that have been modified to employ phage DNA or the expression control sequences; and the like.

For example in a baculovirus expression system, both non-fusion transfer vectors, such as, but not limited to pVL941 (BamHI cloning site Summers), pVL1393 (BamHI, SmaI, XbaI, EcoRI, NotI, XmaIII, BglII and PstI cloning sites; Invitrogen), pVL1392 (BgIII, PstI, NotI, XmaIII, EcoRI, XbalI, SmaI and BamHI cloning site; Summers and Invitrogen) and pBlueBacIII (BamHI, BgIII, PstI, NcoI and HindIII cloning site, with blue/white recombinant screening, Invitrogen), and fusion transfer vectors such as, but not limited to, pAc700(BamHI and KpnI cloning sites, in which the BamHI recognition site begins with the initiation codon; Summers), pAc701 and pAc70-2 (same as pAc700, with different reading frames), pAc360 (BamHI cloning site 36 base pairs downstream of a polyhedrin initiation codon; Invitrogen (1995)) and pBlueBacHisA, B, C (three different reading frames with BamHI, BgIII, PstI, NcoI and HindIII cloning site, an N-terminal peptide for ProBond purification and blue/white recombinant screening of plaques; Invitrogen (220) can be used.

Mammalian expression vectors contemplated for use in the invention include vectors with inducible promoters, such as the dihydrofolate reductase promoters, any expression vector with a DHFR expression cassette or a DHFR/methotrexate co-amplification vector such as pED (PstI, SalI, SbaI, SmaI and EcoRI cloning sites, with the vector expressing both the cloned gene and DHFR; Kaufman, 1991). Alternatively a glutamine synthetase/methionine sulfoximine co-amplification vector, such as pEE14 (HindIII, XbaII, SmaI, SbaI, EcoRI and BclI cloning sites in which the vector expresses glutamine synthetase and the cloned gene; Celltech). A vector that directs episomal expression under the control of the Epstein Barr Virus (EBV) or nuclear antigen (EBNA) can be used such as pREP4 (BamHI, SfiI, XhoI, NotI, NheI, HindIII, NheI, PvuII and KpnI cloning sites, constitutive RS)-LTR promoter, hygromycin selectable marker; invitrogen), pCEP4 (BamHI, SfiI, XhoI, NotI, NheI, HindIII, NheI, PvuII and KpnI cloning sites, constitutive hCMV immediate early gene promoter, hygromycin selectable marker; Invitrogen), pMEP4 (KpnI, PvuI, NheI, HindIII, NotI, XhoI, SfiI, BamHI cloning sites, inducible methallothionein IIa gene promoter, hygromycin selectable marker, Invitrogen), pREP8 (BamHI, XhoI, NotI, HindIII, NheI and KpnI cloning sites, RSV-LTR promoter, histidinol selectable marker, Invitrogen), pREP9 (KpnI, NheI, HindIII, NotI, XhoI, SfiI, BamHI cloning sites, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen).

Selectable mammalian expression vectors for use in the invention include, but are not limited to, pRc/CMV (HindIII, BstXI, NotI, SbaI and ApaI cloning sites, G418 selection, Invitrogen), pRc/RSV (HindII, SpeI, BstXI, NotI, XbaI cloning sites, G418 selection, Invitrogen) and the like. Vaccinia virus mammalian expression vectors (see, for example Kaufman 1991 that can be used in the present invention include, but are not limited to, pSC11 (SmaI cloning site, TK- and β-gal selection), pMJ601 (SalI, SmaI, AflI, NarI, BspMII, BamHI, ApaI, NheI, SacII, KpnI and HindIII cloning sites; TK- and β-gal selection), pTKgpF1S (EcoRI, PstI, SalII, AccI, HindII, SbaI, BamHI and Hpa cloning sites, TK or XPRT selection) and the like.

Yeast expression systems that can also be used in the present include, but are not limited to, the non-fusion pYES2 vector (XbaI, SphI, ShoI, NotI, GstXI, EcoRI, BstXI, BamHI, SacI, KpnI and HindIII cloning sites, Invitrogen), the fusion pYESHisA, B, C (XbalI, SphI, ShoI, NotI, BstXI, EcoRI, BamHI, SacI, KpnI and HindIII cloning sites, N-terminal peptide purified with ProBond resin and cleaved with enterokinase; Invitrogen), pRS vectors and the like.

Consequently, mammalian and typically human cells, as well as bacterial, yeast, fungi, insect, nematode and plant cells an used in the present invention and may be transfected by the nucleic acid or recombinant vector as defined herein.

Examples of suitable cells include, but are not limited to, VERO cells, HELA cells such as ATCC No. CCL2, CHO cell lines such as ATCC No. CCL61, COS cells such as COS-7 cells and ATCC No. CRL 1650 cells, W138, BHK, HepG2, 3T3 such as ATCC No. CRL6361, A549, PC12, K562 cells, 293 cells, Sf9 cells such as ATCC No. CRL1711, Cv1 cells such as ATCC No. CCL70 and JURKAT cells such as ATCC No. Tib152.

Other suitable cells that can be used in the present invention include, but are not limited to, prokaryotic host cells strains such as *Escherichia coli*, (e.g., strain DH5-α), *Bacillus subtilis, Salmonella typhimurium*, or strains of the genera of *Pseudomonas, Streptomyces* and *Staphylococcus*, parasites like *Apicomplexan* parasites (*Plasmodia, Toxoplasma, Cryptosporidia*), *Leishmania* or *Trypanosoma*.

Further suitable cells that can be used in the present invention include yeast cells such as those of *Saccharomyces* such as *Saccharomyces cerevisiae* or *Prombe*.

The above-described motifs and peptides are involved. in binding Bcl-$x_L$ and Bcl-w to PP1c and are thus targeting subunits involved in control of all PP1 binding. Thus, due to their implication in PP1 binding, these motifs are important for the regulation of any disease concerned with phosphatase regulation in all types of cells including all eukaryotic and prokaryotic cells including muscle, heart, liver, lung, brain cells, thymocytes, blood and the like. Plant and bacterial cells are also encompassed in the present invention since the PP1 is found in many different types of plant and bacterial cells. Yeast cells are also encompassed by the present invention. In fact any cell that contains PP1 is encompassed by the present invention.

More importantly, this regulation can effect the downstream regulation of, for example, hepatic glycogen synthesis which in turn would lower blood glucose levels and thus treat diabetes in which hyperglycemia is a severe problem. Thus, the present invention relates to treating diabetes by administering to an animal in need of such treatment a pharmaceutically acceptable amount of the peptides of the present invention which are described in detail within.

In yet another embodiment, the present invention relates to the administration of the peptides of the present invention to normalize high blood pressure. A decrease in phosphorylation of the PP1 complex activates the smooth muscle myosin light chains and hence relaxes smooth muscles (see, Uehata et al., 1997). Therefore, the present invention also relates to administering to an animal a pharmaceutically effective amount of the peptides of the present invention described within to prevent or treat hypertension.

In yet another embodiment the present invention relates to treating neurological disorders by modulating neurological receptors and ion channels. Therefore, the present invention also relates to treating neurological disorders by administering to an animal in need of such treatment a pharmaceutically effective amount of the peptides of the present invention described within to prevent or treat the neurological disorders, such as Parkinson's disease.

More specifically, the present invention relates to treating Alzheimer's disease. Phosphorylation is known to play a role in effecting the β-amyloid precursor which causes the plagues in Alzheimer's disease. Thus, the present invention relates to treating Alzheimer's disease by administering to an animal in need of such treatment a pharmaceutically effective amount of the peptides of the present invention described within to prevent or treat Alzheimer's disease.

In yet another embodiment, the present invention relates to treating viral or microbial infections and more specifically herpes simplex virus, *Myocbacterium tuberculosis* and AIDS by administering to an animal in need of such treatment a pharmaceutically effective amount of the peptides of the present invention described within to prevent or treat the viral infection.

The present invention is especially useful for treating AIDS since both TAT and reverse transcriptase of the HIV-1 virus could be PP1 binding proteins.

In yet another embodiment, the present invention relates to treating parasitic infections such as malaria, *theileria* or *cryptospofidium* by administering to an animal in need of such treatment a pharmaceutically effective amount of the peptides of the present invention described within to prevent or treat these parasitic infections.

The above-mentioned treatments involve administering to an animal in need of such treatment a pharmaceutically acceptable amount of a peptide or a set of peptides which mimics both motifs M1 and M2 and which inhibits the Bcl-$x_L$/PP1c, the Bcl-w/PP1c, or the Bcl-2/Bad/PP1c interactions. For example, a set of peptides comprising the R (NWGRIVAFFSF) (SEQ ID NO: 6) peptide and the F (GDEFELRYRRAF) (SEQ ID NO: 7) peptide, analogues of these peptides or their functional equivalents in a pharmaceutically acceptable vehicle can be administered to said animal.

In another embodiment the present invention relates to pharmaceutical compositions which comprises a peptide or a set of peptides which mimics both motifs M1 and M2 and which inhibits the Bcl-$x_L$/PP1c, the Bcl-w/PP1c, or the Bcl-2/Bad/PP1c interactions. Such a composition can for example comprise the R (NWGRIVAFFSF) (SEQ ID NO: 6) peptide and the F (GDEFELRYRRAF) (SEQ ID NO: 7) peptide, analogues of these peptides or their functional equivalents in a pharmaceutically acceptable vehicle.

The pharmaceutically acceptable vehicle includes, but is not limited to, saline, adjuvants and the like, discussed more extensively above.

The present invention is not limited to solely administering the peptides described within as a "neat" pharmaceutical composition, but also as a pharmaceutical composition in gene therapy, using vectors that encode polypeptides according to the present invention.

More specifically ex vivo and in vitro gene therapy is part of the present, invention. In this respect, any of the methodologies relating to gene therapy available within the art can be used in the practice of the present invention such as those described by Goldspiel et al *Clin. Pharm.* 12 pgs. 488-505 (1993).

Delivery of the therapeutic nucleic acid into a patient can be direct in vivo gene therapy (i.e., the patient is directly exposed to the nucleic acid or nucleic acid-containing vector) or indirect ex vivo gene therapy (i.e., cells are first transformed with the nucleic acid in vitro and then transplanted into the patient).

For example for in vivo gene therapy, an expression vector containing the nucleic acid is administered in such a manner that it becomes intracellular; i.e., by infection using a defective or attenuated retroviral or other viral vectors as described, for example in U.S. Pat. No. 4,980,286 or by Robbins et al, Pharmacol. Ther., 80 No. 1 pgs. 35-47 (1998).

The various retroviral vectors that, are known in the art are such as those described in Miller et al. (*Meth. Enzymol.* 217 pgs. 581-599 (1993)) which have been modified to delete those retroviral sequences which are not required for packaging of the viral genome and subsequent integration into host cell DNA. Also adenoviral vectors can be used which are advantageous due to their ability to infect non-dividing cells and such high-capacity adenoviral vectors are described in Kochanek (*Human Gene Therapy*, 10, pgs. 2451-2459 (1999)). Chimeric viral vectors that can be used are those described by Reynolds et al. (*Molecular Medicine Today*, pgs. 25-31 (1999)). Hybrid vectors can also be used and are described by Jacoby et al. (*Gene Therapy*, 4, pgs. 1282-1283 (1997)).

Direct injection of naked DNA or through the use of microparticle bombardment (e.g., Gene Gun®; Biolistic, Dupont) or by coating it with lipids can also be used in gene therapy. Cell-surface receptors/transfecting compounds or through encapsulation in liposomes, microparticles or microcapsules or by administering the nucleic acid in linkage to a peptide which is known to enter the nucleus or by administering it in linkage to a ligand predisposed to receptor-mediated endocytosis (See Wu & Wu, J. Biol. Chem., 262 pgs. 4429-4432 (1987)) can be used to target cell types which specifically express the receptors of interest.

In another embodiment a nucleic acid ligand compound can be produced in which the ligand comprises a fusogenic viral peptide designed so as to disrupt endosomes, thus allowing the nucleic acid to avoid subsequent lysosomal degradation. The nucleic acid can be targeted in vivo for cell specific endocytosis and expression by targeting a specific receptor such as that described in WO92/06180, WO93/14188 and WO 93/20221. Alternatively the nucleic acid can be introduced intracellularly and incorporated within the host cell genome for expression by homologous recombination (See Zijlstra et al, *Nature*, 342, pgs. 435-428 (1989)).

In ex vivo gene therapy, a gene is transferred into cells in vitro using tissue culture and the cells are delivered to the patient by various methods such as injecting subcutaneously, application of the cells into a skin graft and the intravenous injection of recombinant blood cells such as hematopoietic stem or progenitor cells.

Cells into which a nucleic acid can be introduced for the purposes of gene therapy include, for example, epithelial cells, endothelial cells, keratinocytes, fibroblasts, muscle. cells, hepatocytes and blood cells. The blood cells that can be used include, for example, T-lymphocytes, B-lymphocytes, monocytes, macrophages, neutrophils, eosinophils, megakaryotcytes, granulocytes, hematopoietic cells or progenitor cells and the like.

The polypeptides and complexes of polypeptides of the invention also find use in raising antibodies. Thus, the present invention provides antibodies, which can be monoclonal or polyclonal.

Thus, the polypeptides and complexes of the invention can be used as an immunogen to generate antibodies which specifically bind such an immunogen. Antibodies of the invention include, but are not limited to polyclonal, monoclonal, bispecific, humanized or chimeric antibodies, single chain antibodies, Fab fragments and F(ab') fragments, fragments produced by a Fab expression library, anti-idiotypic (anti-Id) antibodies, and epitope-binding fragments of any of the above. The term "antibody" as used herein refers to immunoglobulin molecules and immunologically active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

In the production of antibodies, screening for the desired antibody can be accomplished by techniques known in the art, e.g., ELISA (enzyme-linked immunosorbent assay). For example, to select antibodies which recognize a specific domain of a polypeptide of the invention (e.g., a Selected Interacting Domain), one can assay generated hybridomas for a product which binds to a polypeptide fragment containing such domain. For selection of an antibody that specifically binds a first polypeptide homolog but which does not specifically bind to (or binds less avidly to) a second polypeptide homolog, one can select on the basis of positive binding to the first polypeptide homolog and a lack of binding to (or reduced binding to) the second polypeptide homolog.

For preparation of monoclonal antibodies (mAbs) directed toward a polypeptide of the invention or a fragment or an analog thereof, any technique which provides for the production of antibody molecules by continuous cell lines in culture may be used. For example, the hybridoma technique originally developed by Kohler and Milstein (1975, Nature 256: 495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies can be of any immunoglobulin class including IgG, IgM, IgE, IgA, IgD and any subclass thereof. The hybridoma producing the mAbs of the invention can be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g., human-mouse chimeras). A chimeric antibody is a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity. determining regions (CDRs) from the non-human species and a framework region from a human immunoglobulin molecule. (See, e.g., Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European, Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239: 1534; and Beidler et al., 1988, J. Immunol. 141:4053-4060.

Completely human antibodies are particularly desirable for therapeutic treatment of human patients. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g., all or a portion of a BPI of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) Bio/technology 12:899-903).

The antibodies of the present invention can also be generated using various phage display methods known in the art. In phage display methods, functional antibody domains are displayed on the surface of phage particles which carry the polynucleotide sequences encoding them. More specifically, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

The invention further provides for the use of Dispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, EMBO J. 10:3655-3659.

According to a different approach, antibody variable domains with the desired binding specificities (antibody-antigen combining sites) are fused to immunoglobulin constant domain sequences. The fusion can be with an immunoglobulin heavy chain constant domain, comprising at least part of the hinge, CH2, and CH3 regions. Generally, the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In another embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology, 1986, 121:210.

The invention provides functionally active. fragments, derivatives or analogs of the anti-polypeptide immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in an embodiment, the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')2 fragments and Fab fragments. Antibody fragments which recognize specific epitopes can be generated by known techniques. F(ab')2 fragments consist of the variable region, the light chain constant region and the CH1 domain of the heavy chain and are generated by pepsin digestion of the antibody molecule. Fab fragments are generated by reducing the disulfide bridges of the F(ab')2 fragments. The invention also provides heavy chain and light chain dimmers of the antibodies of the invention, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* can be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g., a peptide bond), at either the N-terminus or the C-terminus to an amino acid sequence of another protein (or portion thereof, preferably at least 10, 20 or 50 amino acid portion of the protein) that is not the immunoglobulin. In an embodiment, the immunoglobulin, or a fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are either modified, i.e., by the covalent attachment of any type of molecule as long as such covalent attachment that does not impair immunospecific binding. For example, but not by way of limitation, the derivatives and analogs of the immunoglobulins include those that have been further modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the analog or derivative can contain one or more nonclassical amino acids.

The foregoing antibodies can be used in methods known in the art relating to the localization and activity of the polypeptides of the invention, e.g., for imaging or radioimaging these proteins, measuring levels thereof in appropriate physiological samples, in diagnostic methods, etc. and for radiotherapy.

The antibodies of the invention can be produced by any method known in the art for the synthesis of antibodies, for instance, by chemical synthesis or by recombinant expression, and are preferably produced by recombinant expression technique.

Recombinant expression of antibodies, or fragments, derivatives or analogs thereof, requires construction of a nucleic acid that encodes the antibody. If the nucleotide sequence of the antibody is known, a nucleic acid encoding the antibody can be assembled from chemically synthesized oligonucleotides (e.g., as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody can be obtained by cloning the antibody. If a clone containing the nucleic acid encoding the particular antibody is not available, but the sequence of the antibody molecule is known, a nucleic acid encoding the antibody can be obtained from a suitable source (e.g., an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen can be generated by any method known in the art, for example, by immunizing an animal, such as a rabbit, to generate polyclonal antibodies or, by generating monoclonal antibodies. Alternatively, a clone encoding at least the Fab portion of the antibody may be obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid encoding at least the variable domain of the antibody molecule is obtained, it can be introduced into a vector containing the nucleotide sequence encoding the constant region of the antibody molecule (see, e.g., PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCT based methods, etc.

In addition, techniques developed for the production of "chimeric antibodies" (Morrison et al., 1984, Proc. Natl. Acad. Sci. 81:851-855; Neuberger et al., 1984, Nature 312: 604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g., humanized antibodies.

Once a nucleic acid encoding an antibody molecule of the invention has been obtained, the vector for the production of the antibody molecule can be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro. recombinant DNA techniques, synthetic techniques, and in vivo genetic recombination. See, for example, the techniques described in Sambrook et al. (1990, Molecular Cloning, A Laboratory Manual, 2d Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention can be either bacterial cells such as *Escherichia coli*, or eukaryotic cells, especially for the expression of whole recombinant antibody molecule. More specifically, mammalian cells such as Chinese hamster ovary cells (CHO), in conjunction with a vector such as the major intermediate early gene promoter element from human cytomegalovirus is an effective expression system for antibodies (Foecking et al., 198, Gene 45:101; Cockett et al., 1990, Bio/Technology 8:2).

A variety of host-expression vector systems can be utilized to express an antibody molecule of the invention. Such host-expression systems represent vehicles by which the coding sequences of interest can be produced and subsequently purified, but also represent cells which can, when transformed or transfected with the appropriate nucleotide coding sequences, express the antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing the antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited to, the E. coli expression vector pUR278 (Ruther et al., 1983, EMBO J. 2:1791), in which the antibody coding sequence can be ligated individually into the vector in frame with the lacZ coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter). In mammalian host cells, a number of viral-based expression systems (e.g., an adenovirus expression system) can be utilized.

As discussed above, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein.

For long-term, high-yield production of recombinant antibodies, stable expression is useful. For example, cells lines that stably express an antibody of interest can be produced by transfecting the cells with an expression vector comprising the nucleotide sequence of the antibody and the nucleotide sequence of a selectable (e.g., neomycin or hygromycin), and selecting for expression of the selectable marker. Such engineered cell lines can be useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two expression vectors of the invention, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it can be purified by any method known in the art for purification of an antibody molecule, for example, by chromatography (e.g., ion exchange chromatography, affinity chromatography such as with protein A or specific antigen, and sizing column chromatography), centrifugation, differential solubility, or by any other standard technique for the purification of proteins.

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

In another embodiment, antibodies of the invention or fragments thereof are conjugated to a diagnostic or therapeutic moiety. The antibodies can be used for diagnosis or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}I$ and $^{99}Tc$.

Antibodies of the invention or fragments thereof can be conjugated to a therapeutic agent or drug moiety to modify a given biological response. The therapeutic agent or drug moiety is not to be construed as limited to classical chemical therapeutic agents. For example, the drug moiety can be a protein or polypeptide possessing a desired biological activity. Such proteins can include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

The present invention not only relates to the peptides, their-use and administration in pharmaceutically acceptable vehicles, but also to methods of using the peptides and the motifs as disclosed within.

More specifically, the present invention has utilization for several methods in which the peptides described within are used for the following purposes:

(1) A method of identifying a PP1-interacting polypeptide or protein, comprising detecting in the sequence of said polypeptide or protein, the presence of two PP1-binding motifs M1 and M2.

(2) A method of screening compounds that interacts with PP1 regulators, comprising:
  (a) immobilizing peptides described herein on a support; and
  (b) testing the interaction of said compounds with said immobilized peptides.

(3) A method of screening compounds that interact with PP1, comprising:
  (a) obtaining antibodies to peptides within the description of the present invention; and
  (b) testing the interaction of said compounds with said antibodies.

(4) A method for testing molecules that inhibit or enhance the PP1 activity or change its localization by interaction, said method comprising:
  (a) immobilizing peptides described within on a support; and
  (b) testing the interaction of said compounds with said immobilized peptides.

Also encompassed by the present invention are drugs that after using the methods of the present invention are found to inhibit and/or enhance PP1 activity, PP1c activity or localization by interaction.

Besides methods, the present invention relates to kits. The kits comprise, but are not limited to, peptides or sets of peptides which mimic both the motifs M1 and M2 and which are able to inhibit the Bcl-$x_L$/PP1c, the Bcl-w/PP1c, or the Bcl-2/Bad/PP1c interactions, wherein the motif M1 has the sequence FXX[RK]X[RK], and the motif M2 has the sequence [RK]VX[FW] or [RK]XVX[FW], wherein X is any amino acid. Such kits can, for example, comprise the peptides R (NWGRIVAFFSF) (SEQ ID NO: 6) and F (GDEFELRYRRAF) (SEQ ID NO: 7). These peptides may be immobilized on any solid support, described above, and which includes resins, microstar wells, glass chips and the like.

In yet another embodiment the present invention relates to a kit containing antibodies to peptides which mimic both the motifs M1 and M2 and which are able to inhibit the Bcl-$x_L$/PP1c, the Bcl-w/PP1c, or the Bcl2/Bad/PP1c interactions. These antibodies can have been raised against the peptides R (NWGRIVAFFSF) (SEQ ID NO: 6) and F (GDEFELRYRRAF) (SEQ ID NO: 7) peptides, the analogues of these peptides or their functional equivalents.

Besides the peptides or the antibodies, the kits of the present invention also include reagents for interpreting the interaction. Such reagents are, known in the art and described above and in Sambrook (supra).

In yet another embodiment, the present invention concerns a method of screening cells to find PP1 interactions in the cells, said method comprising either using antibodies against the motifs M1 and M2 or peptides including these motifs or their functional equivalents.

The present invention thus also relates to a new phosphatase-derived drug therapy based on the intracellular delivery of peptides with a sequence or sequences surrounding the PP1/PP2 binding sites (M1 and M2 motifs) identified in some interacting proteins. This drug therapy approach, derived from chemical genetics (Gure, 2000), would specifically inhibit the interaction of some medically important target proteins with PP1/PP2A.

This therapeutic strategy, called "Peptidic knockout" of PP1/PP2 pathways has the basis in two recent results. The first result was the identification of a putative PP1 signature. Thus, from the characterization of two distinct PP1 binding motifs in Bcl-2 proteins and their existence in most PP1 binding proteins, it can be concluded that the combinatory presence of the motifs can be used as a predictive signature for PP1 binding. Thus, the web site called "PP1 signature" (in preparation at the Institut Pasteur) that contains all putative PP1 sequences derived from a Swisprot library can be used to identify putative PP1-binding targets of interest.

The second result was the identification of PP2A binding sites in five proteins. The PP2A binding sites of a viral encoded (HIV-1) Vpr and a parasitic Ck2a encoded by Theileria were recently mapped. From the data obtained it can be said that the intracellular delivery of some peptides mimicking these PP2A-binding sequences lead to apoptosis in tumors (Hela, Jurkat, S) or infected cells (Vpr or HIV-1 or Theileria).

EXAMPLES

The following examples can be performed using the materials and methods described below:

1. Materials and Methods 1.1. Cells and Culture

Ts1αβ is a murine T cell line expressing the α and β chains of the IL-2 receptor (Pitton et al, 1993) that can be propagated independently in IL-2, IL-4 or IL-9. Cells were cultured in RPMI-1640 supplemented with 5% heat-inactivated fetal calf serum 2 mM glutamine, 10 mM Hepes, 0.55 mM arginine, 0.24 mM asparagine, 50 µM 2-ME and 60 U/ml of IL-4.

1.2. Lymphokines, Antibodies, Reagents and Plasmids

Murine rIL-4 or supernatant of a HeLa subline transfected with pKCRIL-4.neo was used as a source of murine IL-4. Anti-Bcl-$x_L$ and anti-Bcl-w antibody were from Calbiochem (La Jolla, Calif.), Transduction Laboratories (Lexington, Ky.) or StressGen Biotechnology (Victoria, Canada). Specific anti-PP1c was from UBI (Lake Placid, N.Y.), Calbiochem or Transduction Laboratories. Anti-Histones antibody was from Chemicon International (Temecula, Calif.). Anti-14-3-3 protein antibody was from UBI (Lake Placid, N.Y.). Anti-Bad serine 112 and 136 were from New England BioLabs (Beverly, Mass.) and serine 155 was from Cell Signaling Technology (Beverly, Mass.). Anti-Raf antibody was from Transduction Laboratories. Anti-Pser and pan-Ras antibody were from Calbiochem. Recombinant PP1c protein was from Calbiochem. Mito 2813 (anti-mitochondrial pyruvate dehydrogenase) was provided by Dr Serrano, Centro Nacional de Biotecnologia (Madrid).

1.3. Immunoprecipitation and Western Blot

Cells (1×10$^7$) were IL-4-stimulated or -deprived and lysed for 20 min at 4° C. in lysis buffer (50 mM Tris HCl pH 8, 1% NP40, 137 mM NaCl, 1 mM MgCl$_2$, 1 mM CaCl$_2$, 10% glycerol and protease inhibitors cocktail). Digitonin or detergent free buffers were also used for immunoprecipitation. For phosphorylation analysis, the buffer was also supplemented with phosphatase inhibitors cocktail. Lysates were immunoprecipitated with the Appropriate antibody and Protein A Sepharose was added. Alliteratively, cells were lysed in Laemmli sample buffer and protein extracts separated by SDS-PAGE, transferred to nitrocellulose, blocked and incubated with primary antibody. Membrane was washed and incubated. with PO-conjugated secondary antibody. Proteins were developed using the ECL.

1.4. In vitro Phosphatase Assay

IL-4-stimulated cells (1×10$^7$) were lysed in lysis buffer, supernatants were immunoprecipitated with the corresponding antibody, followed by incubation with Protein A Sepharose. Immunoprecipitates were washed with phosphatase buffer (50 mM Tris HCl, pH 7.5, 0.1% 2-ME, 0.1 mM EDTA and 1 mg/ml BSA) and mixed with [$^{32}$P] phosphorylase a, diluted in phosphatase buffer supplemented with caffeine. The reaction was incubated (40 min at 30° C.), stopped with 200 µl 20% TCA and centrifuged. A total of 185 µl of the supernatant were used to estimate the generation of free phosphate liberated from [$^{32}$P] phosphorylase a.

1.5. Peptide Synthesis

Peptides comprising the R/K X V/I X F (R) or F X X R X R (F) motif of Bcl-w and Bcl-$x_L$, as well as the mutated peptides (see FIG. 8A for sequence) were prepared by automated spot synthesis into an aminoderivatized cellulose membrane. Membrane was blocked, incubated with purified PP1c and, after several washing steps, incubated with anti-PP1c antibody, followed by PO-conjugated secondary antibody. Spots were developed using the ECL system.

R (NWGRIVAFFSF) (SEQ ID NO: 6), F (GDEFELRYR-RAF) (SEQ ID NO: 7) or R* (NWGRIAAAFSF) (SEQ ID NO: 8) peptides were synthetized on an automated multiple peptide synthesizer using the solid-phase procedure and standard Fmoc chemistry. The purity and composition of the peptides was confirmed by reverse-phase high performance liquid chromatography and by amino acid analysis.

1.6. Protein-Protein Interaction Competition

The interaction Bcl-w/PP1c and Bcl-$x_L$/PP1c was competed by the R, F, or R* peptides. Lysates from IL-4-stimulated cells were immunoprecipitated with anti-Bad antibody and Protein A Sepharose was added. The interaction Bcl-w/PP1c and Bcl-$x_L$/PP1c was competed by incubation with R. F or R* peptides (30 min, room temperature). After washing, immunoprecipitates were either assayed for protein phosphatase activity or transferred to nitrocellulose and blotted with the corresponding antibody.

1.7. Sense and Antisense Oligonucleotides

The phosphothioate analogous of the oligonucleotides from Bcl-$x_L$ and Bcl-w, including the ATG initiation codon were purchased from Isogen Bioscience. The sequence of the sense and antisense oligonucleotides are as follow. Sense Bcl-$x_L$, ATG TCT CAG AGC AAC (SEQ ID NO: 9); antisense Bcl-$x_L$, GTT GCT CTG AGA CAT (SEQ ID NO: 10); sense Bcl-w, ATG GCG ACC CCA GCC (SEQ ID NO: 11); antisense Bcl-w, GGC TGG GGT CGC CAT (SEQ ID NO: 12).

Figure 1A:
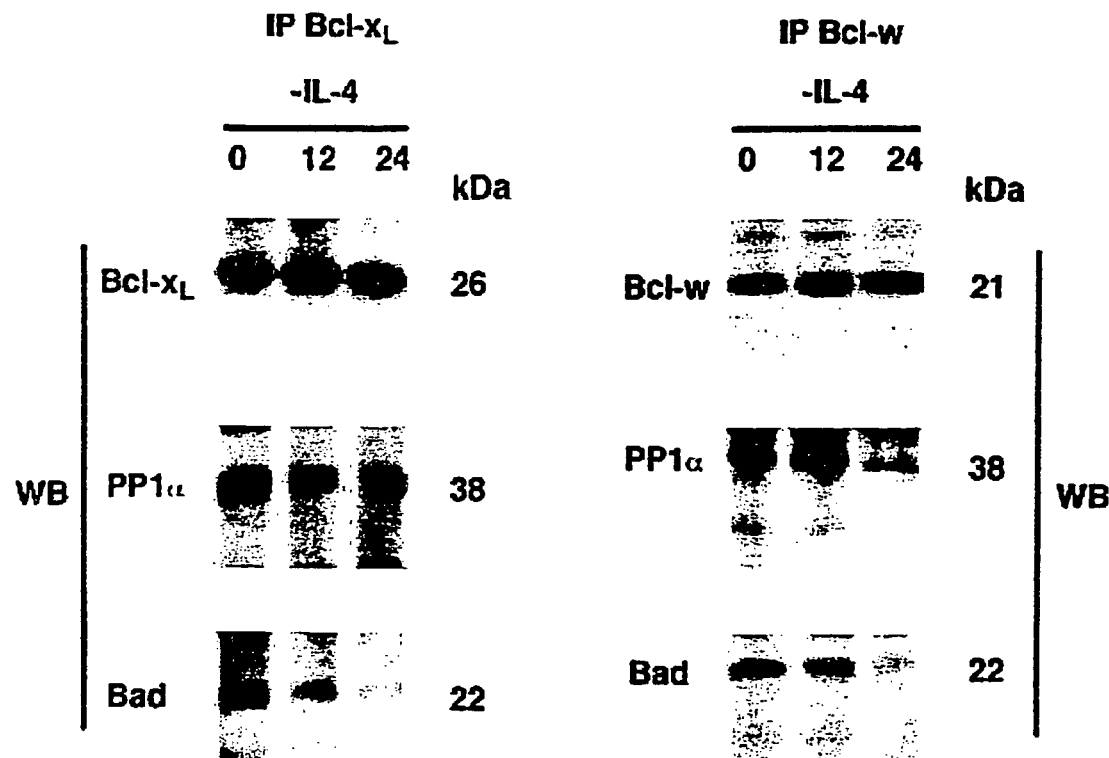
FIG. 1. Association of Bcl-$x_L$ and Bcl-w to PP1c and Bad.
Figure 1B:
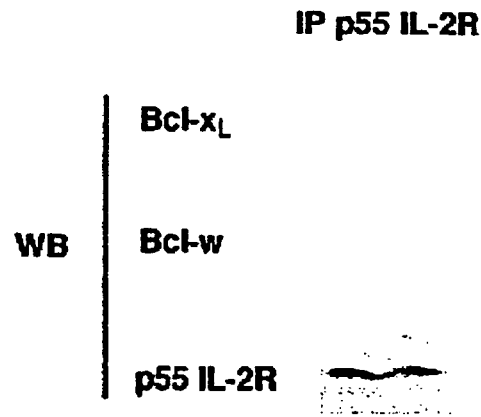
Figure 2A:
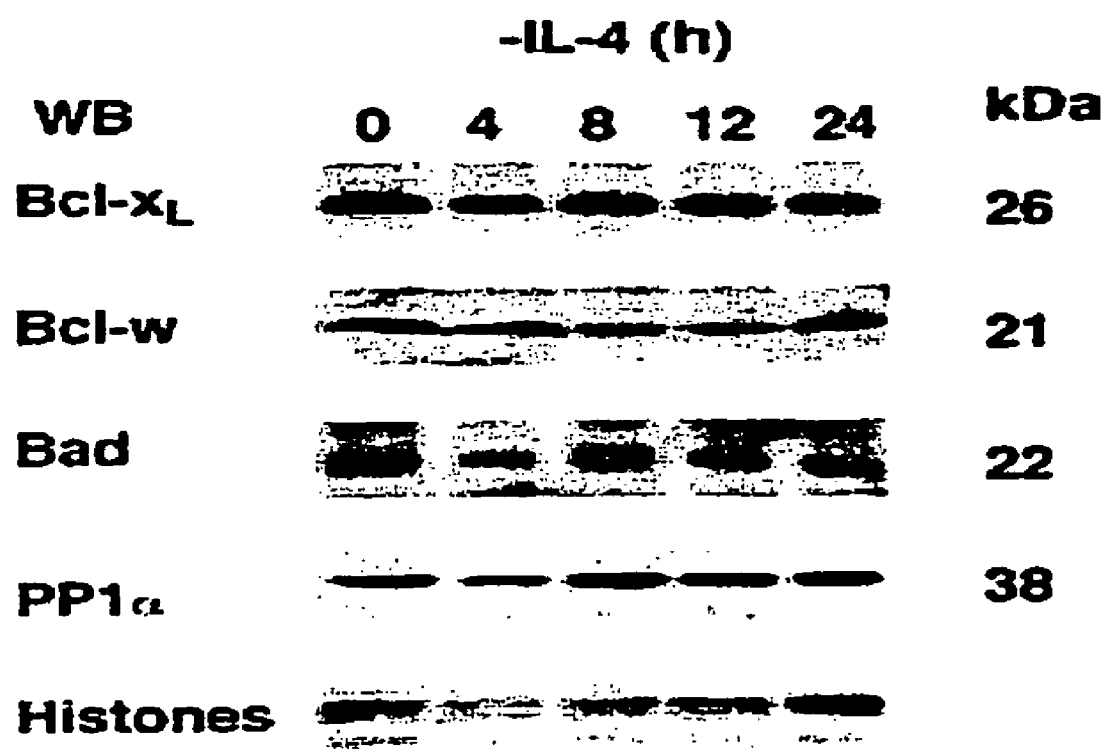
Figure 2B:
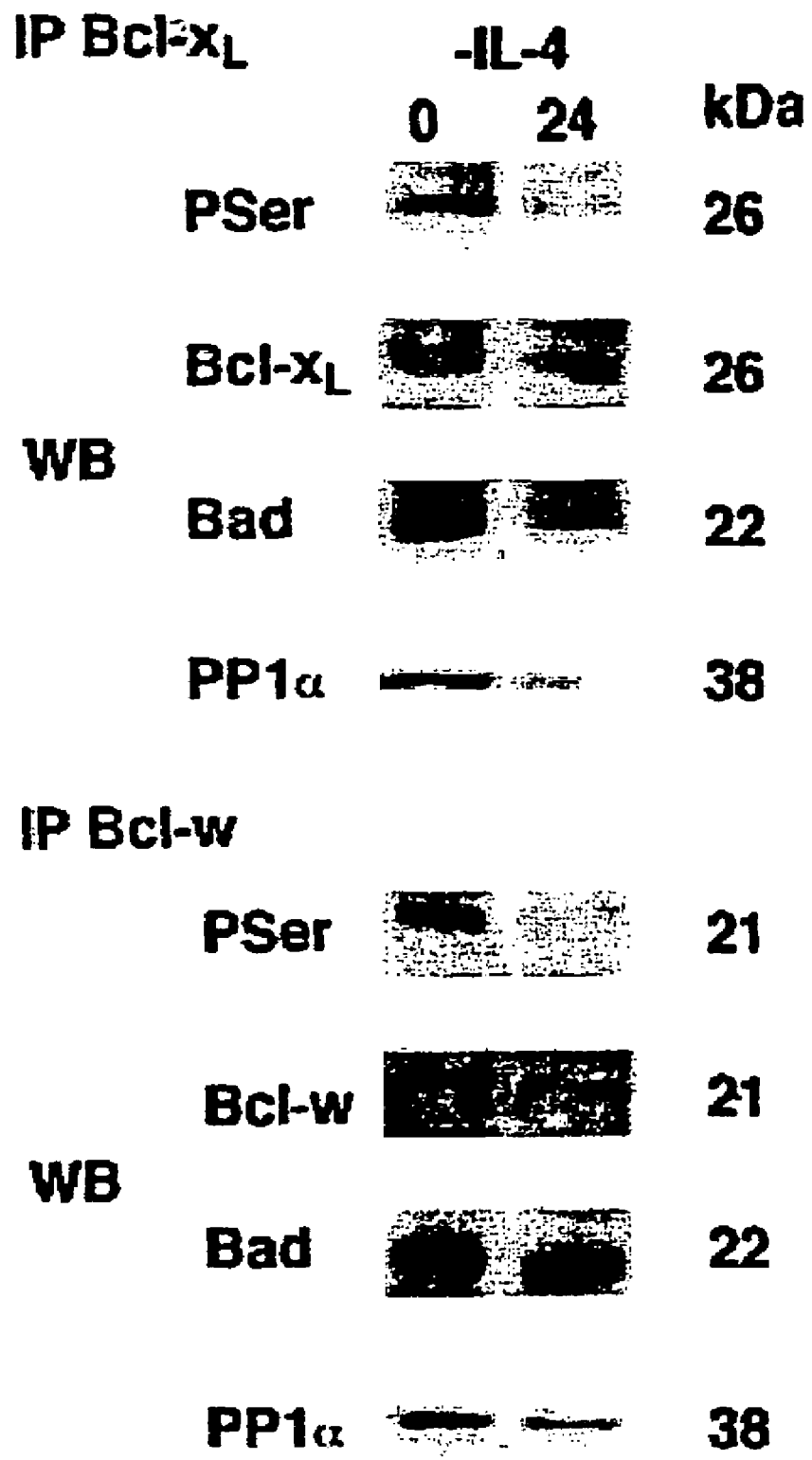
Figure 2C:
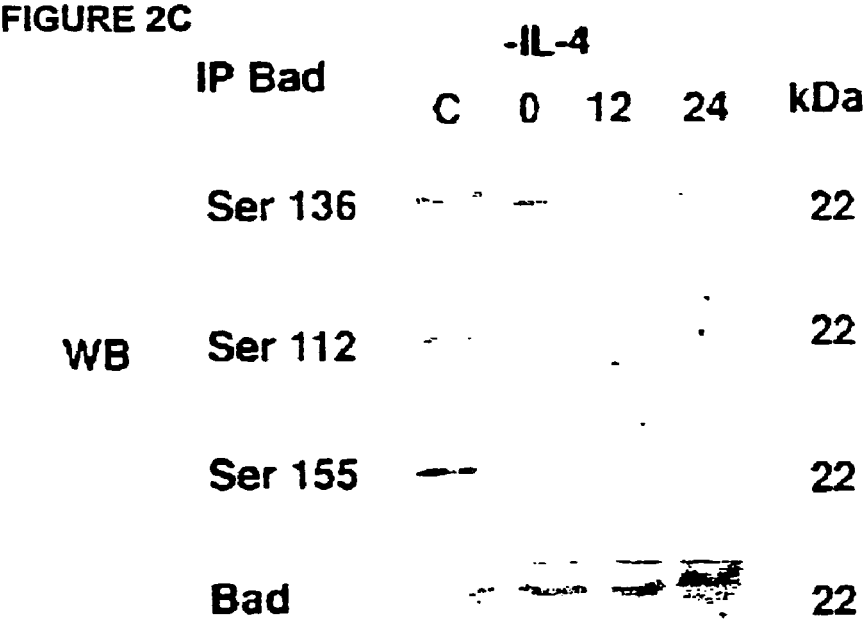
Figure 2D:
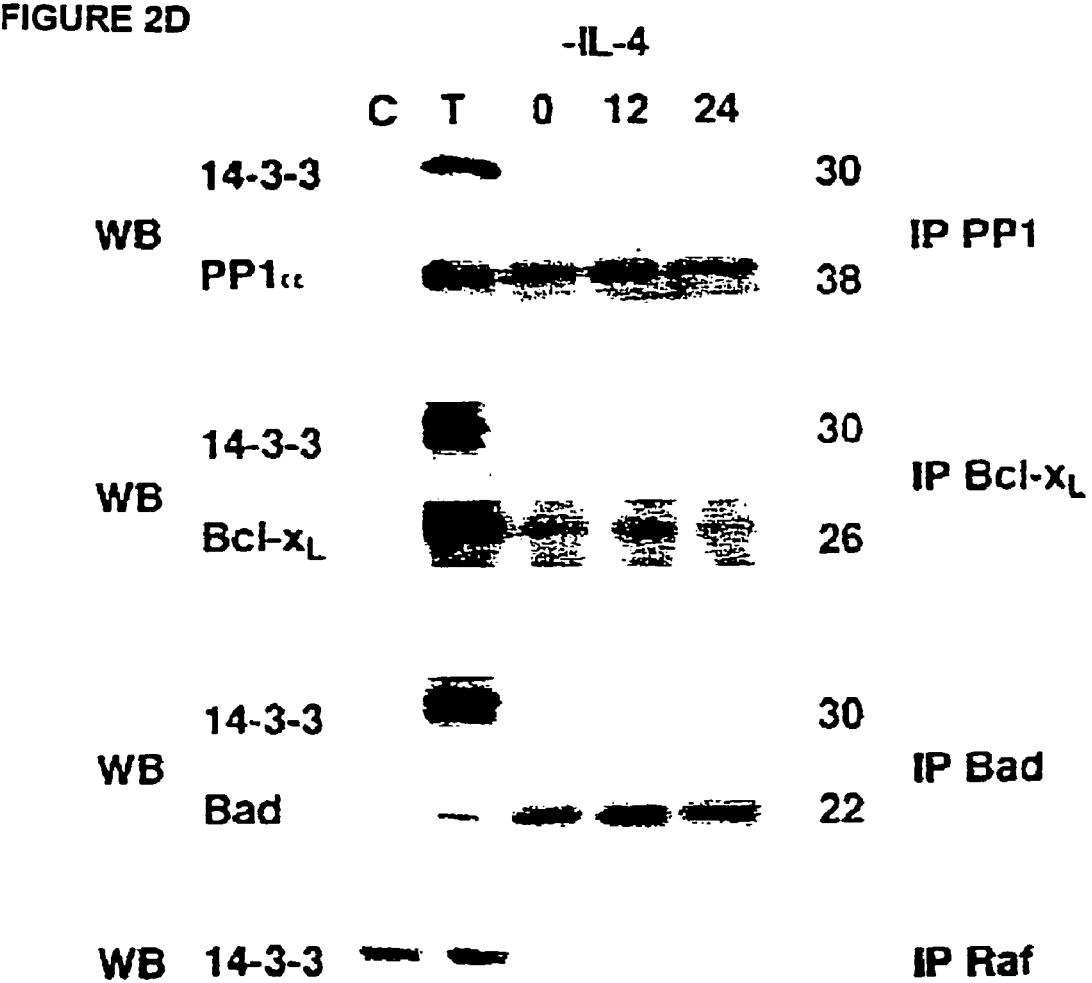

2. Experimental Results 2.1. Identification of Bcl-w and Bcl-$x_L$ as PP1c-interacting proteins It was previously shown that anti-apoptotic molecule Bcl-2 is a targeting subunit of the serine/threonine phosphatase PP1c in IL-2-stimulated TS1αβ cells and that the sequence of Bcl-2 interacting with PP1c is the R/K X V/I X F motif (Ayllón et al, 2001). Given that Bcl-$x_L$ and Bcl-w also contain the well conserved R/K X V/I X F motif observed in Bcl-2, the possibility that anti-apoptotic molecules Bcl-$x_L$ and Bcl-w may be as well associated to PP1c in IL-4-stimulated TS1αβ a cells, which do not express Bcl-2 and express Bcl-$x_L$ and Bcl-w was explored. Reciprocal Co-immunoprecipitation experiments of cytoplasmic proteins under ILA4-stimulation or -deprivation conditions using specific antibodies was performed. PP1c and Bad were detected by Western blot in anti-Bcl-$x_L$ immunoprecipitates of IL-4 stimulated cells, decreasing throughout the starvation period (FIG. 1A). Probing the membrane with anti-Bcl-$x_L$ antibody showed similar levels in all conditions analyzed. PP1c and Bad were also detected in anti-Bcl-w immunoprecipitates of IL-4 stimulated cells, diminishing after lymphokine deprivation (FIG. 1A). Membrane was also probed with anti-Bcl-w antibody, showing similar levels. Immunoprecipitation for cytoplasmic lysates with an irrelevant antibody, anti-p55 IL-2R chain, was not able to detect those associations (FIG. 1B). Similarly, Bcl-$x_L$, Bcl-w and PP1c were detected in Bad immunoprecipitates and the interaction among these proteins was also observed by immunoprecipitation of detergent-free lysates as well as in cytoplasmic proteins isolated by digitonin lysis (data not shown). These associations were also observed in freshly isolated thymocytes (FIG. 1C). Given that the number of Bcl-$x_L$/PP1c/Bad and Bcl-w/PP1c/Bad complexes decreases after IL-4-deprivation, down-regulation of the expression of any of the proteins involved in the formation of the complex was analyzed. Thus, the total expression of Bcl- $x_L$, Bcl-w, PP1c and Bad in IL-4-stimulated or -deprived TS1αβ cells was analyzed. All analyzed proteins were expressed in IL-4-stimulated or -deprived cells (FIG. 2). As an internal control of protein loading, membranes were probed with anti-Histones antibody. As the number of aggregates decreases after IL-4-deprivation without modification of total expression of the proteins of the complex, post-translational modifications of Bcl-$x_L$ or Bcl-w may affect the formation of the trimolecular complex was then analyzed. The status of serine phosphorylation of Bcl-$x_L$ and Bcl-w was next analyzed. Cytoplasmic extracts from IL-4-stimulated or -deprived cells were immunoprecipitated with anti-Bcl-$x_L$ or anti-Bcl-w and blotted with anti-Pser, anti-PP1c, anti-Bad, anti-Bcl-w and anti-Bcl-$x_L$ specific antibodies (FIG. 3). Serine phosphorylation of. Bcl-$x_L$ and Bcl-w was observed in control IL-4-stimulated cells, decreasing after IL-4 deprivation. In agreement with results in FIG. 1, the level of Bad and PP1c associated to Bcl-$x_L$ and Bcl-w diminishes upon lymphokine deprivation. This result suggests a correlation between serine phosphorylation of Bcl-$x_L$ and Bcl-w and formation of trimolecular complexes.

Figure 4A:
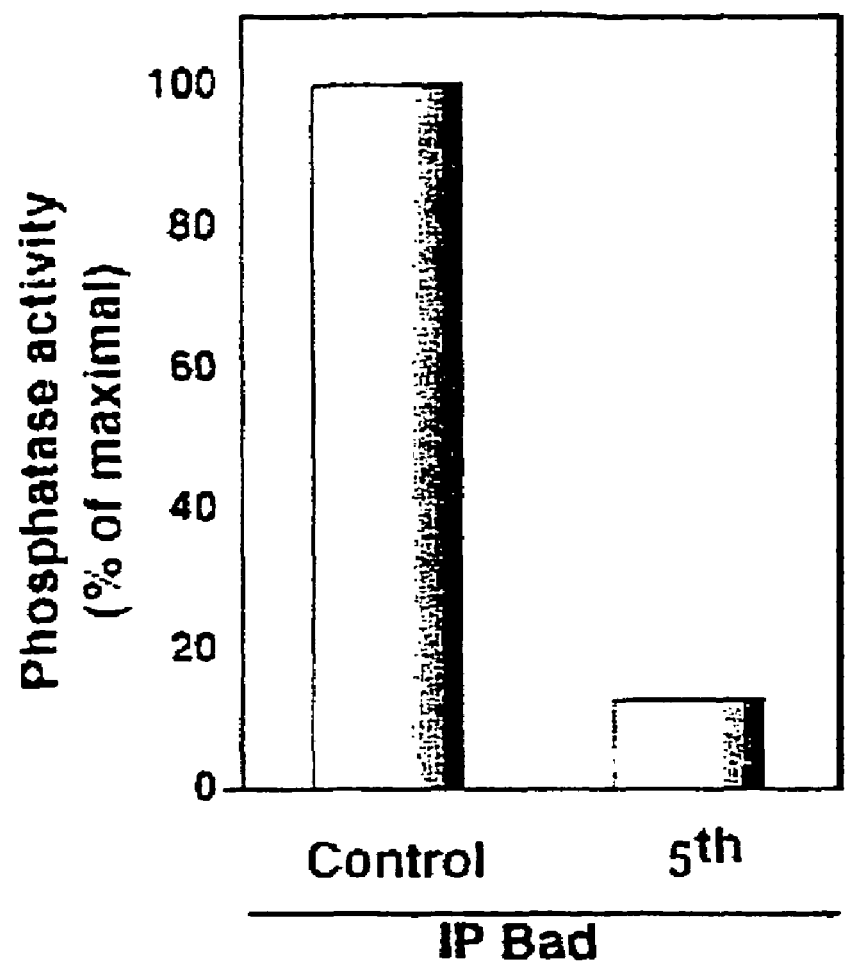
Figure 4B:
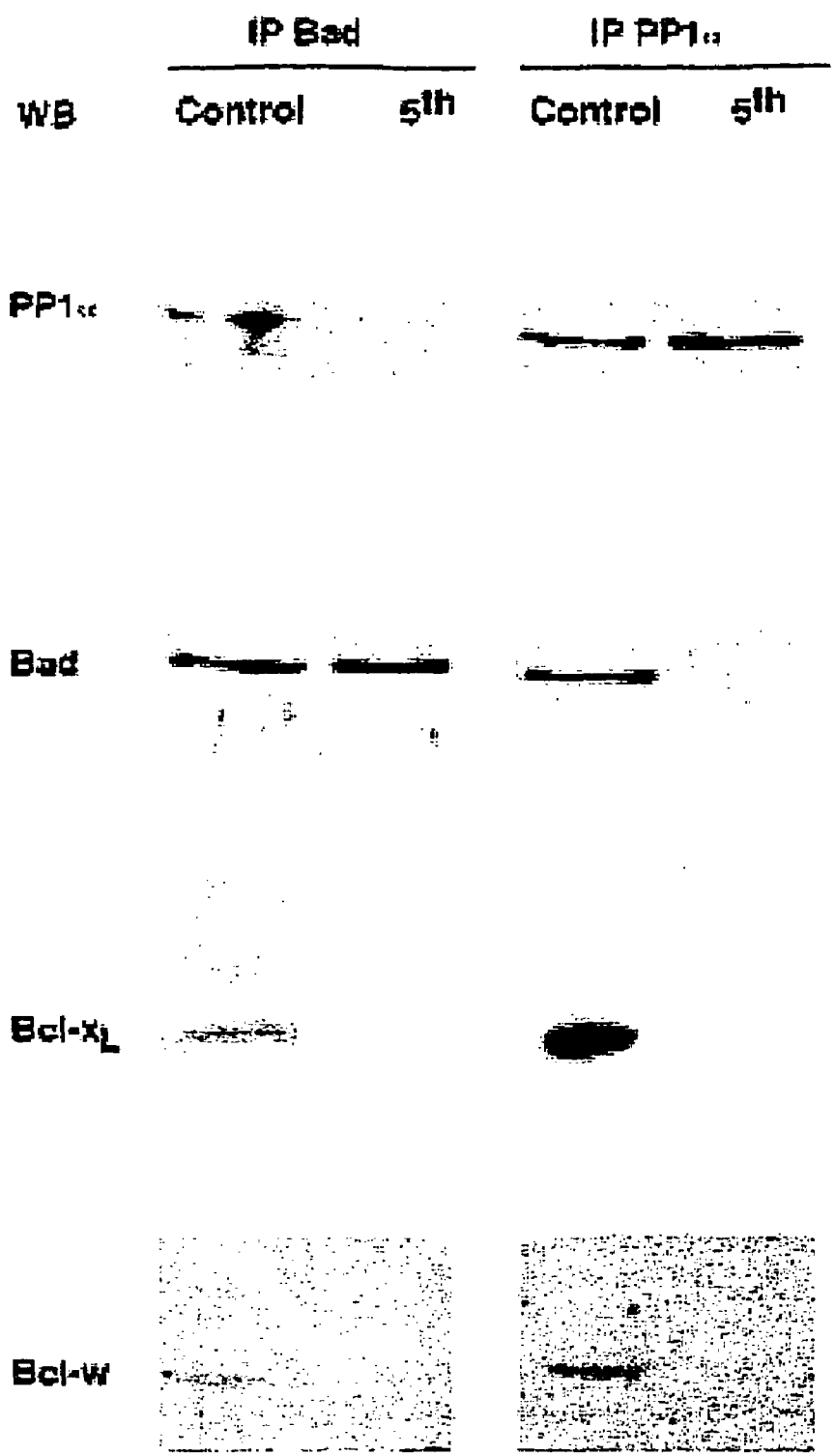

It was recently shown that IL-2, as well as IL-3, induces serine phosphorylation of Bad (Ayllón et al, 2000). FIG. 4A shows that IL-4 induces Bad phosphorylation at serine 136 but not at serines 112 and 155. Moreover, IL-4-deprivation induces serine 136 dephosphorylation of Bad. IL-2 stimulated cells (C, ser 112 and 136 phosphorylation) or COS (C, ser 155 phosphorylation) cells overexpressing Bad were used as a positive controls. IL-3-induced serine phosphorylation of Bad results in its association to the 14-3-3 protein, abolishing interaction with Bcl-x (Zhou et al, 2000). FIG. 4B shows that serine phosphorylation of Bad in response to IL-4 does not result in binding to 14-3-3 protein. This protein was detected in total extracts from control IL-4 stimulated cells (lane T) and was not observed neither in PP1c, nor in Bcl-$x_L$ or Bad immunoprecipitates of IL-4-stimulated or -deprived cells. As an internal control, the interaction of Raf and the 14-3-3 protein in Raf immunoprecipitates is shown (FIG. 4B).

FIG. 5A shows phosphatase activity in Bcl-$x_L$, Bcl-w and Bad immunoprecipitates of IL-4-stimulated cells. The enzymatic activity in the immunoprecipitates was measured using $^{32}$P-labeled phosphorylase a as substrate. It is interesting to notice that phosphatase activity detected in Bcl-$x_L$ and Bcl-w immunoprecipitates nearly corresponds to the phosphatase activity observed in Bad immunoprecipitates. To confirm that this phosphatase activity was due to PP1c, enzymatic activity was estimated in Bad or Bcl-w immunoprecipitates from IL-4-stimulated cells in the presence of different okadaic acid (OA) concentrations (FIG. 5B). OA concentrations that inhibit type 2A activity ($10^{-9}$ M) had no effect on Bad- or Bcl-w-associated phosphatase activity in vitro. Addition of $10^{-8}$ M OA to Bcl-w or Bad immunoprecipitates results in ~50% inhibition of phosphatase activity, which is strongly reduced after addition of $10^{-6}$ M OA (FIG. 5B). The effect of OA on phosphatase activity was also estimated in supernatants of Bad and Bcl-w immunoprecipitates. OA concentrations that had no effect on enzymatic activity in Bad and Bcl-w immunoprecipitates ($10^{-9}$ M) shows ~50% inhibition in the supernatant, as expected from an association of type 1 and type 2A activities (FIG. 5B). The selective effect of OA suggests that the phosphatase activity observed in Bad and Bcl-w immunoprecipitates is PP1c.

2.2. Bcl-w and Bcl-$x_L$ are New Targeting Subunits of PP1c

It was recently shown that Bcl-2 is a targeting subunit of PP1c (Ayllón et al, 2001). Given that Bcl-w and Bcl-$x_L$ are also associated to PP1c and that sequence of binding site of Bcl-2 to PP1c is conserved in Bcl-$x_L$ and Bcl-w, it was hypothesized that these anti-apoptotic molecules may be new targeting subunits of PP1c. To test this hypothesis, Bcl-$x_L$ and Bcl-w was depleted by sequential anti-Bcl-$x_L$+Bcl-w immunoprecipitation of cytoplasmic extracts of IL-4 stimulated cells. Supernatant from the fourth anti-Bcl-$x_L$+Bcl-w immunoprecipitation was immunoprecipitated with anti-Bad antibody (5th) and phosphatase activity estimated (FIG. 6A). Traces of Bad-associated phosphatase activity were detected in Bcl-$x_L$ and Bcl-w depleted extracts compared to the high level of activity observed in control anti-Bad immunoprecipitates of IL-4-stimulated cells. Given that in the absence of Bcl-$x_L$ and Bcl-w significant Bad-associated phosphatase activity was not detected, the possibility that these anti-apoptotic molecules may control targeting of PP1c to Bad was explored. For this purpose, anti-Bad immunoprecipitations were made in cytoplasmic extracts of IL-4 stimulated cells or in extracts depleted of Bcl-$x_L$ and Bcl-w (5th). PP1c, Bcl-$x_L$ and Bcl-w were detected in control ant-Bad immunoprecipitates and were not observed in anti-Bad immunoprecipitates from extracts depleted of Bcl-$x_L$ and Bcl-w (FIG. 6B). In a reciprocal experiment, Bad, Bcl-$x_L$ and Bcl-w were detected in anti-PP1c immunoprecipitates of control cells and were not observed in PP1c immunoprecipitates from extracts depleted of Bcl-$x_L$ and Bcl-w (FIG. 6B). This result suggests that Bcl-$x_L$ and Bcl-w are needed for association of PP1c to Bad.

2.3. Determination of Bcl-$x_L$ and Bcl-w Binding Site to PP1c

It has been described that R/K X V/I X F motif is shared by most of the PP1c targeting subunits (21, 23). It was shown that PP1c targeting subunit Bcl-2 also shares this conserved motif (Ayllón Ct al, 2001). Interestingly, Bcl-$x_L$ and Bcl-w sequences also contain this motif (FIG. 7B). To analyze whether this sequence of Bcl-$x_L$ and Bcl-w was involved in binding to PP1c, we generated nitrocellulose-immobilized peptides of Bcl-$x_L$ and Bcl-w protein containing this motif. Membrane was incubated with purified PP1c protein. FIG. 7B shows the sequences interacting with PP1c. The R/K X V/I X F motif, present in Bcl-$x_L$ and Bcl-w, interact with PP1 c and its mutation in critical V and F residues strongly reduces binding of Bcl-$x_L$ and Bcl-w to PP1c (FIG. 7B). Analysis of the Bcl-2 binding sites to PP1c showed, in addition to R/K X V/I X F motif, two sequences (FSRRYR (SEQ ID NO: 5) and FTARGR (SEQ ID NO: 5), that bind PP1c (Ayllón et al, 2001). Interestingly, similar sequences were as well observed in Bcl-$x_L$ and Bcl-w (FIG. 7A). FELRYR (SEQ ID NO: 5) and FETRFR (SEQ ID NO: 5) sequences of Bcl-$x_L$ and Bcl-w respectively also interacts with PP1c and its mutation inhibit binding to PP1c, although the affinity depends on the type of point mutation (FIG. 7B). The interacting consensus F X X R X R motif was determined by sequence comparison of Bcl-2, Bcl-$x_L$ and Bcl-w.

To conclusively confirm that R/K X V/I X F and F X X R X R motifs are involved in binding of Bcl-$x_L$ and Bcl-w to PP1c, competition experiments in trimolecular complexes were performed. Lysates from IL-4-stimulated cells were immunoprecipitated with anti-Bad antibody and the interaction Bcl-$x_L$/PP1c and Bcl-w/PP1c was competed using R* (NWGRIAAAFSF) (SEQ ID NO: 8), R (NWGRIVAFFSF) (SEQ ID NO: 6) or F (GDEFELRYRRAF) (SEQ ID NO: 7) peptides (FIG. 8A). Bcl-$x_L$, Bcl-w and PP1c were detected in control anti-Bad immunoprecipitates, as well as in anti-Bad immunoprecipitates treated with R* peptide. The amount of Bcl-$x_L$, Bcl-w and PP1c associated to Bad decreases after competition with F or R peptide, being almost undetectable upon competition of Bad immunoprecipitates with F+R peptides (FIG. 8A). Similar level of Bad is observed in control or peptide-treated anti-Bad immunoprecipitates. Finally, to confirm that Bcl-$x_L$ and Bcl-w are targeting subunits of PP1c, we estimated phosphatase activity in control or peptide-treated Bad immunoprecipitates. Phosphatase activity was detected in control or R* peptide-treated immunoprecipitates (FIG. 8B), decreasing upon competition of the interaction with F or R peptides. Enzymatic activity was strongly decreased upon competition with R and F peptides. As an internal control, FIG. 8C shows the phosphatase activity in control or peptide-treated Bad immunoprecipitates. The concentration of F or R peptide used was twice the concentration used in F+R peptide-treated immunoprecipitates. As in FIG. 8B, phosphatase activity was drastically reduced upon treatment of Bad immunoprecipitates with F+R peptides. Taken together, these results illustrate that Bcl-$x_L$ and Bcl-w, as well as Bcl-2, are PP1c targeting subunits.

2.4. Inhibition of PP1c Enzymatic Activity Blocks Apoptosis

As IL-4-deprivation correlates with Bad dephosphorylation and apoptosis, it was hypothesized that inhibition of phosphatase activity by okadaic acid (OA) treatment may prevent Bad dephosphorylation and apoptosis. Treatment of the cells with 1 µM OA in the absence of IL-4 prevented Bad dephosphorylation at serine 136 (FIG. 9A). No changes in total Bad expression were observed after OA treatment, suggesting that OA does not affect protein expression. In addition, IL-4-deprived cells treated with 1 µM OA for 6 h showed significant reduction in the fraction of apoptotic cells compared with untreated cells (FIG. 9B). Finally, inhibition of Bcl-$x_L$ and Bcl-w expression by antisense oligonucleotide treatment of cells also induces apoptosis in IL-4-stimulated cells (FIG. 9C). The inhibition of Bcl-$x_L$ and Bcl-w expression upon antisense oligonucleotide treatment was estimated by Western blot.

3. Bio-Informatic Results—Predictive Signature for PP1 Interactions: Combinatorial Presence of [RK]VxF or [RK]xVxF and F-x-x-[RK]-x-[RK] Motifs in Characterized PP1 Binding Proteins The combinatorial presence of these two PP1 binding motifs suggests a general mechanism wherein sequential binding to PP1c through one of these motifs may favor binding through the second motif and allow catalytic function. Furthermore these motifs could also represent a predictive signature to identify new potential PP1 binding proteins. To partially test this concept, a bioinformatic analysis was performed by using "prose" (Katja Shuerer, IP) program in the Swissprot Release40 library (October 2001) that contains 101602 non redundant protein sequences.

As shown in Table 1A, the search for the presence of only one consensus indicates that 19.47% of the sequences in the library contain [RK]VXF or [RK]xVxF motifs and 16% contain the Bcl-2-like motif F-x-x-[RK]-x-[RK]. In contrast, consistently with the notion of predictive signature, analysis of combinatorial presence of both PP1 binding motifs [RK]VxF or [RK]xVxF and F-x-x-[RK]-x-[RK] revealed only 4013 positives sequences, corresponding to 3.94% of the library (Table 1B). In addition if the F=W equivalency (usually accepted for [RK]Vx[FW]/[RK]xVx[FW] motifs) is applied, 4783 positives sequences corresponding to 4.7 of the library were found. In addition, the occasionally equivalency between R/K and Q slightly increases the number of positives proteins (5769 sequences corresponding to 5.67%).

Furthermore, as expected, these sequences include all the known PP1 interacting proteins of the Bcl-2 family (not shown). Together this analysis indicates that around 5% of protein sequences share the two putative PP1 binding motifs in their sequence. Interestingly, statistical analysis suggests the distance separating the two PP1 binding motifs is comprises between 0 and 180 aa for 50% of the proteins (FIG. 11). In addition, a more detailes analysis reveals a major peak representing 22.3% of positive sequences (897 sequences for a total of 4013) that correspond to a 0-50 aa interval between the two motifs. These data are consistent with the observation that a distance of 36 aa separates the two binding motifs in BH1 and BH3 domains of Bcl-2/Bcl-w and Bcl-$x_L$ proteins (not shown).

On the basis of this analysis, the Institut Pasteur is creating and will maintain in order a new web site "PP1signature" which contains all the sequences selected from the Swissprot Release 40 library corresponding to proteins haboring the two PP1 binding motifs. By. simply entering the name of a protein or an accession number or through blast analysis, everyone will immediately know if the protein has a putative PP1 signature. In addition, the user will immediately identify the sequence encompassing the two putative PP1 binding motifs.

Most characterised PP1-binding proteins share the two motifs and can be identified in the web site (table 2). To validate this proposal of "predictive signature strategy," four candidates were randomly selected and their association PP1 by simple co-immunoprecipitation experiments was confirmed (FIG. 10B).

TABLE 1A

| ONE MOTIF | POSITIVE SEQUENCES | % TOTAL LIBRARY |
|---|---|---|
| F-x-x-R-x-R | 4,074 | 4 |
| F-x-x[RK]-[RK] | 16,260 | 16 |
| [RK]-V-x-F | 8,895 | 8.76 |
| [RK-x-V-x-F | 9,935 | 9.48 |
| [RK]-V-x-F or [RK]-X-V-x-F | 16,273 | 16.02 |
| [RK]-V-x-[FW] or [RK}-x-V-x-[FW] | 19,787 | 19.48 |

TABLE 1B

| TWO MOTIFS | POSITIVE SEQUENCES | % TOTAL LIBRARY |
|---|---|---|
| [RK]-V-x-F or [RK]-x-V-x-F + F-x-x-R-x-R | 1,025 | 1 |
| [RK]-V-x-F or [RK]-x-V-x-F + F-x-x-R-x-R | 4,013 | 3.94 |
| [RK]-V-x-[FW] or [RK]-x-V-x-[FW] + F-x-x-[RK]-x-[RK] | 4,783 | 4.70 |
| [RKQ]-V-x-F/W or [RKQ]-x-V-x-F/W + F-x-x-[RK]-x-[RK] | 5,769 | 5.67 |

TABLE 2A

Two putative PP1 binding sequences in characterized PP1-interacting proteins

| Protein/gene | motif 1 | Residues | motif 2 | Residues |
|---|---|---|---|---|
| *Yeast* | | | | |
| GIP2 (homolog of GM) 6320895 | QFERKNEKLD (SEQ ID NO: 85) | 12-18 | LIRSKSVHFDQA (SEQ ID NO: 86) | 216-227 |
| GIP2h/YIL045 S49933 | SLEFLHKPR RLS (SEQ ID NO: 87) | 55-60 | QRSKSVHFD (SEQ ID NO: 88) | 191-202 |
| *YAL014 L05146 | DLFNERRQRR (SEQ ID NO: 89) | 110-116 | MPTRHNVRWEEN (SEQ ID NO: 90) | 45-56 |
| REG2 6319525 | RSWFKARKRRDI (SEQ ID NO: 91) | 152-157 | KPRERHIKFNDN (SEQ ID NO: 92) | 163-174 |
| *Mammalian* | | | | |
| Mouse PTG AAB49689 | RRNFVN KLKPL (SEQ ID NO: 93) | 28-38 | NQAKKRVVFADS (SEQ ID NO: 94) | 56-67 |
| | | | TVKVKNVSFEKK | 149-160 |
| *GL CAA77083 Y | LDFRNRLQTN (SEQ ID NO: 95) | 121-130 | KKVKKRVSFAND (SEQ ID NO: 96) | 56-67 |
| Human R5 4885559 | RH FVNKLKPLKS (SEQ ID NO: 97) | 48-60 | NQAKKRVVFADS (SEQ ID NO: 98) | 79-90 |
| U5 AAC60216 | TCFRPRLRGS (SEQ ID NO: 99) | 101-110 | SQKKKRVVFADM (SEQ ID NO: 100) | 61-72 |
| *Splicing factor PSF* | | | | |
| P23246 | GEVFINKGKGF (SEQ ID NO: 101) | 324-334 | RGRQLRVRFATH (SEQ ID NO: 102) | 358-369 |
| Ribosomal Protein L5 P22451 | QVKFRRRREG (SEQ ID NO: 103) | 17-26 | YFKRYQVKFRRR (SEQ ID NO: 104) | 12-23 |
| GRP-78 P20029 | EDFKAKKKEL (SEQ ID NO: 105) | 615-620 | RITPSYVAFTPE (SEQ ID NO: 106) | 61-72 |
| Human 110pRB P06400 | SVFMQRLKTNILQ (SEQ ID NO: 107) | 758-770 | IDEVKNVYFKNF (SEQ ID NO: 108) | 285-296 |
| | | | VLKVSWITFLLA (SEQ ID NO: 109) | 190-201 |
| AKAPs (AKAP149/AKAP220/Yotiao) | LQFELRYRPV (SEQ ID NO: 110) | 250-255 | TTKAVMFAK (SEQ ID NO: 111) | 141-145 |
| Hsp-90-α (Hsp 86) P07901 | DLFENRKKKN (SEQ ID NO: 112) | 353-358 | VRRVFIM (SEQ ID NO: 113) | 367-370 |
| Human MYPT2 4505319 | FFKNEKMLY (SEQ ID NO: 114) | 331-340 | RRGSPRVRFEDG (SEQ ID NO: 115) | 48-59 |
| Human I-2 CAA55475 | RQFEMKRKLHY (SEQ ID NO: 116) | 128-138 | Not detected | |

*These two sequences correspond to a higher degenerated consensus (F-X-X-R/K-X-R/K/Q)
Consensus  F-X-X-R/K-X-R/K    R/K-X-V/I-X-F
           Or R/K-V/I-X-F

Example 4

β Amyloid Precusor as a New PP1 Interacting Protein

Fibrillar amyloid deposits are defining pathological lesions in Alzheimer's brain diseases and are thought to mediate neuronal death. Amyloid is composed of a 39 to 42 amino acid protein fragment of the amyloid precursor protein (APP). Because deposition of fibrillar amyloid in vitro has been shown to be dependent upon the APP concentration, reducing or inhibiting the release of APP is a therapeutic target.

The β-amyloid precursor (APP) is overexpressed in PC12 cells treated by NGF, by transfection of a cDNA-encoding the β-amyloid precursor (APP) according to the methods of Sambrook et al, supra.

The cells expressing the β-amyloid precursor are then incubated with a penetrating peptide corresponding to the punitive PP1 binding site such as the motif M1 having the sequence FXX[RK]X[RK] and the M2 motif [RK]VX[FW] or [RKXVX[FW], where X is any amino acid.

The presence of amyloid is tested using monoclonal antibodies or a

REFERENCES

Aggen, J. B., Nairn, A. C. and Chamberlin, R., Regulation of protein phosphatase. *Chem. and Biol.* 2000. 7: R13-R23.

Ayllón, V., Cayla, X, Garcia, A., Roncal, F; Fernández, R; Albar, J. P; Martinez-A, C., Rebollo, A. (2001). Bcl-2 targets protein phosphatase 1α to Bad. *J Immunol;* 166: 7345-7352.

Ayllón, V., Martinez-A., C., Garcia, A., Cayla, X. and Rebollo, A., Protein phosphatase 1α is a Ras-activated Bad phosphatase that regulates IL-2 deprivation-induced apoptosis. *EMBO J.* 2000. 19: 2237-2246.

Beullens M, Van Eynde A, Vulsteke V, Connor J, Shenolikar S, Stalmans W, Bollen Molecular determinants of nuclear protein phosphatase-1 regulation by NIPP-1. *J Biol Chem.* 1999 May 14; 274:14053-61.

Boise, L. H., González-García, M., Postema, C. E., Ding, L. Y., Lindsten, T., Turka, L. A., Mao, X. H., Núñez, G. and Thompson, C. B., Bcl-x, a Bcl-2 related gene that functions as a dominant regulator of apoptotic cell death. *Cell* 1993. 74: 597-608.

Bollen M. Combinatorial control of protein phosphatase-1. TIBS 26 (2001),426-431

Chao, D. T. and Korsmeyer, S. J., Bcl-2 family: regulators of cell death. *Annu. Rev. Immunol.* 1998.16: 395-419.

Colledge, M. and Scott, J. D., AKAPs: from structure to function. *Trends Cell. Biol.* 1999. 9: 216-221.

Datta, S. R., Dukek, H., Tao, X., Masters, S., Fu, H., Gotoh, Y. and Greenberg, M. E., Akt phosphorylation of Bad couples survival signals to the cell intrinsic death machinery. *Cell* 1997. 91: 231-241.

Datta, S. R., Katsov, A., Hu, L., Petros, A., Fesik, S. W., Yaffe, M. B. and Greenberg, M. E., 14-3-3 proteins and survival kinases cooperate to inactivate Bad by BH3 domain phosphorylation. *Mol. Cell.* 2000. 6: 41-51.

Del Peso, L., Garcia, M. G., Page, C., Herrera, R. and Nuñez, G., IL-3-induced phosphorylation of Bad through the protein kinase Akt. *Science* 1997. 278: 687-689.

Deng, X., Ito, T., Carr, B., Mumby, M. and May, W. S., Reversible phosphorylation of Bcl-2 following IL-3 or bryostatin 1 is mediated by direct interaction with protein phosphatase 2A. *J. Biol. Chem.* 1998. 273: 34157-34163.

Egloff, M. P., Johnson, D. J., Moorhead, G., Cohen, P. T. W., Cohen, P. and Barford, D., Structural basis for the recognition of regulatory subunits by the catalytic subunit of protein phosphatase 1. *EMBO J.* 1997. 16: 1876-1887.

Gibson, L., Holmgreen, S., Huang, D. C. S, Bernard, O., Copeland, N. G., Jenkins, N. A., Sutherland, G. R, Baker, E., Adams, J. M. and Cory, S., Bcl-w, a novel member of the Bcl-2 family promotes cell survival. *Oncogene* 1996.13: 665-675.

Gross, A., McDonnell, J. M. and Korsmeyer, S. J, Bcl-2 gene family and the regulation of programmed cell death. *Genes Dev.* 1999. 13: 1899-1911.

Gura, T. (2000). "A chemistry set for life." *Nature* 407(6802): 282-4.

Hsu, H. Y., Kaipai, L., Zhu, L. and Hsueh, A .J., Interference of Bad induced apoptosis in mammalian cells by 14-3-3 isoforms and P11. *Mol. Endocrinol.* 1997.11: 1858-1867.

Ito, T., Deng, X., Carr, B. and May, W. S., Bcl-2 phosphorylation required for antiapoptotic function. *J. Biol. Chem.* 1997. 272: 11671-11673.

Jacobson, M. D., Apoptosis: Bcl-2-related proteins get connected. *Curr. Biol.* 1997. 7: 277-281.

Korsmeyer, S. J, Bcl-2 family and the regulation of programmed cell death. *Cancer Res.* 1999. 59:1693s-1700s.

McAvoy T, Allen P B, Obaishi H. Nakanishi H, Takal Y, Greengard P, Nairn A C, Hemmings H C Jr. Regulation of neurabin I interaction with protein phosphatase 1 by phosphorylation. *Biochemistry.* 1999. 38:12943-9.

Minn, A. J., Boise, L. H. and Thompson, C. B., Bcl-xs antagonizes the protective effects of Bcl-$x_L$. *J. Biol. Chem.* 1996. 271: 6306-6312.

Núñez, G., Merino, R., Grillot, D. and González-García, M., Bcl-2 and Bcl-x: regulatory switches for lymphoid death and survival. *Immunol. Today* 1994. 15: 582-588.

Ottilie, S. J., Diaz, L., Horne, W., Chang, J., Wang, Y., Wilson, G., Chag, S., Weeks, S., Fritz, L. C. and Oltersdofr, T., Dimerization properties of human Bad. *J. Biol. Chem.* 1997. 272: 30866-30890.

Pitton, C., Rebollo, A., Van Snick, J., Theze, J. and Garcia, A., High affinity and intermediate affinity forms of the IL-2R expressed in an IL-9-dependent murine T cell line deliver proliferative signals via differences in their transduction pathways. *Cytokine* 1993. 5: 362-371.

Rebollo, A, Perez-Sala, D. and Martinez-A., C., Bcl-2 differentially targets K-, N- and H-Ras to mitochondria in IL-2 supplemented or deprived cells: implications in prevention of apoptosis. *Oncogene* 1999. 18: 4930-4939.

Reed, J. C, Bcl-2 family proteins. *Oncogene* 1998. 17: 3225-3236.

Sattler M, Liang H, Nettesheim D, Meadows R P, Harlan J E, Eberstadt M, Yoon H S, Shuker S B, Chang B S, Minn A J, Thompson C B, Fesik S W, Structure of Bcl-$x_L$-Bak peptide complex: recognition between regulators of apoptosis. *Science.* 1997. 275(5302):983-986.

Shenolikar, S., Protein serine/threonine phosphatases, new avenues for cell regulation. *Annu. Rev. Cell Biol.* 1994. 10: 55-86.

White, E., Life, death and the pursuit of apoptosis. *Genes Dev.* 1996. 10: 1-15.

Yaffe M B., Rittinger Katrin, Volinia S., Caron P R., Aitken A., Leffers H., Smerdon S J., Cantley L. C, The Structural Basis for 14-3-3: Phosphopeptide Binding Specificity implicated 14-3-3 as a key regulator of signal transduction events. *Cell* 1997, 91: 961-971.

Zha, J., Harada, H., Osipov, K., Jockel, J., Waksman, G. and Korsmeyer, S. J., Serine phosphorylation of death agonist Bad in response to survival factor results in binding to 14-3-3 protein. *J. Biol. Chem.* 1997. 272: 24101-24104.

Zhou, X. M., Liu, Y., Payne, G., Lutz, R. J. and Chittenden, T., Growth factors inactivate the cell death promoter Bad by phosphorylation of its BH3 domain on serine 155. *J. Biol. Chem.* 2000. 275: 25046-25051.

Zolnierowicz, S. and Bollen, M. Protein phosphorylation and protein phosphatases. *EMBO J.* 2000. 19: 483-488.

What is claimed is:

1. A peptide set consisting of two peptides, consisting of two sequence motifs, M1 and M2,
    wherein each individual peptide consists of a sequence motif,
    wherein M1 is on one peptide and M2 is on another peptide,
    wherein the set of peptides is able to inhibit an interaction selected from the group consisting of Bcl-$x_L$/PP1c, Bcl-w/PP1c, and Bad/PP1c,
    wherein the sequence motif M1 consists of the sequence FXX[RK]X[RK], wherein the sequence motif M2 is a sequence selected from the group consisting of [RK]VX[FW] and [RK]XVX[FW],
    wherein, for the sequence motifs M1 and M2, X is any amino acid,
    wherein for the sequence motifs M1 and M2, the presence of two amino acids surrounded by brackets is a notation meaning that one of the two amino acids within the brackets is present in the motif sequence, and
    wherein, optionally, at least one amino acid residue of at least one of the sequence motifs M1 and M2 is modified by glycosylation, acetylation, phosphorylation, or amidation.

2. A peptide set, consisting of NWGRIVAFFSF (SEQ ID NO: 6) and GDEFELRYRRAF (SEQ ID NO: 7).

3. A method of screening compounds that interact with PP1 regulators, comprising:
    (a) immobilizing the peptide set according to claim 1 on a support; and
    (b) testing the interaction of said compounds with said immobilized peptide set.

4. A pharmaceutical composition comprising the peptide set according to claim 1 or claim 2 and a pharmaceutically acceptable vehicle.

5. A method of preparing a medicament, comprising combining the peptide set of claim 1 and a pharmaceutically acceptable vehicle.

6. A method for testing molecules that inhibit or enhance PP1 activity or change its localisation by interaction, said method comprising:
    (a) immobilizing the peptide set according to claim 1 on a support; and
    (b) testing the interaction of said molecules with said immobilized peptide set.

7. The peptide set of claim 1, wherein at least one of the amino acid residues of at least one of the sequence motifs M1 and M2 is glycosylated, acetylated, phosphorylated or amidated.

8. A peptide consisting of two sequence motifs M1 and M2,
    wherein the peptide is able to inhibit an interaction selected from the group consisting of Bcl-$x_L$/PP1c, Bcl-w/PP1c, and Bad/PP1c;
    wherein the sequence motif M1 consists of the sequence FXX[RK]X[RK];
    wherein sequence motif M2 is a sequence selected from the group consisting of [RK]VX[FW] and [RK]XVX[FW];
    wherein, for the sequence motifs M1 and M2, X is any amino acid,
    wherein for the sequence motifs M1 and M2, the presence of two amino acids surrounded by brackets is a notation meaning that one of the two amino acids within the brackets is present in the motif sequence, and
    wherein at least one amino acid residue of at least one of the sequence motifs M1 and M2 is modified by glycosylation, acetylation, phosphorylation, or amidation.

9. A peptide set consisting of two peptides consisting of two sequence motifs M1 and M2,
    wherein each individual peptide consists of a sequence motif, wherein M1 is on the one peptide and M2 is on the other peptide;

wherein the peptide set is able to inhibit an interaction selected from the group consisting of Bcl-$x_L$/PP1c and Bcl-w/PP1c, wherein the sequence motif M1 consists of the sequence NWGRIVAFFSF (SEQ ID NO: 6)

wherein the sequence motif M2 consists of the sequence GDEFELRYRRAF (SEQ ID NO: 7), and wherein, optionally, at least one amino acid residue of at least one of the sequence motifs M1 and M2 is modified by glycosylation, acetylation, phosphorylation, or amidation.

10. The set of peptides of claim 9, wherein at least one of the amino acid residues on at least one of the sequence motifs M1 and M2 is glycosylated, acetylated, phosphorylated or amidated.

11. A pharmaceutical composition comprising the peptide set of claim 9 and a pharmaceutically acceptable vehicle.

12. A pharmaceutical composition comprising the peptide of claim 8 and a pharmaceutically acceptable vehicle.

* * * * *

SEQUENCE LISTING

<160> NUMBER OF SEQ ID NOS: 116

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 1

Arg Xaa Val Xaa Phe
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 2

Lys Xaa Val Xaa Phe
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 3

Arg Xaa Ile Xaa Phe
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = any amino acid
<220> FEATURE:

```
<221> NAME/KEY: MISC_FEATURE
<222> LOCATION: (4)..(4)
<223> OTHER INFORMATION: Xaa = any amino acid

<400> SEQUENCE: 4

Lys Xaa Ile Xaa Phe
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid

<400> SEQUENCE: 5

Phe Xaa Xaa Arg Xaa Arg
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Asn Trp Gly Arg Ile Val Ala Phe Phe Ser Phe
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 7

Gly Asp Glu Phe Glu Leu Arg Tyr Arg Arg Ala Phe
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

Asn Trp Gly Arg Ile Ala Ala Ala Phe Ser Phe
1               5                   10

<210> SEQ ID NO 9
<211> LENGTH: 15
<212> TYPE: DNA
<213> ORGANISM: Artificial Sequence
<220> FEATURE:
```

```
<223> OTHER INFORMATION: Synthetic Construct

<400> SEQUENCE: 9
atgtctcaga gcaac                                                    15

<210> SEQ ID NO 10
<211> LENGTH: 15
<212> TYPE: DNA
<213> ORGANISM: Artificial Sequence
<220> FEATURE:
<223> OTHER INFORMATION: Synthetic Construct

<400> SEQUENCE: 10
gttgctctga gacat                                                    15

<210> SEQ ID NO 11
<211> LENGTH: 15
<212> TYPE: DNA
<213> ORGANISM: Artificial Sequence
<220> FEATURE:
<223> OTHER INFORMATION: Synthetic Construct

<400> SEQUENCE: 11
atggcgaccc cagcc                                                    15

<210> SEQ ID NO 12
<211> LENGTH: 15
<212> TYPE: DNA
<213> ORGANISM: Artificial Sequence
<220> FEATURE:
<223> OTHER INFORMATION: Synthetic Construct

<400> SEQUENCE: 12
ggctggggtc gccat                                                    15

<210> SEQ ID NO 13
<211> LENGTH: 6
<212> TYPE: PRT
<213> ORGANISM: Artificial sequence
<220> FEATURE:
<223> OTHER INFORMATION: Synthetic Peptide

<400> SEQUENCE: 13

Phe Ser Arg Arg Tyr Arg
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 14

Phe Thr Ala Arg Gly Arg
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 15

Phe Glu Leu Arg Tyr Arg
```

<210> SEQ ID NO 16
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 16

Phe Glu Thr Arg Phe Arg
1               5

<210> SEQ ID NO 17
<211> LENGTH: 10
<212> TYPE: PRT
<213> ORGANISM: Saccharomyces cerevisiae

<400> SEQUENCE: 17

Gln Phe Glu Arg Lys Asn Glu Lys Leu Asp
1               5                   10

<210> SEQ ID NO 18
<211> LENGTH: 12
<212> TYPE: PRT
<213> ORGANISM: Saccharomyces cerevisiae

<400> SEQUENCE: 18

Leu Ile Arg Ser Lys Ser Val His Phe Asp Gln Ala
1               5                   10

<210> SEQ ID NO 19
<211> LENGTH: 12
<212> TYPE: PRT
<213> ORGANISM: Saccharomyces cerevisiae

<400> SEQUENCE: 19

Ser Leu Glu Phe Leu His Lys Pro Arg Arg Leu Ser
1               5                   10

<210> SEQ ID NO 20
<211> LENGTH: 9
<212> TYPE: PRT
<213> ORGANISM: Saccharomyces cerevisiae

<400> SEQUENCE: 20

Gln Arg Ser Lys Ser Val His Phe Asp
1               5

<210> SEQ ID NO 21
<211> LENGTH: 10
<212> TYPE: PRT
<213> ORGANISM: Saccharomyces cerevisiae

<400> SEQUENCE: 21

Asp Leu Phe Asn Glu Arg Arg Gln Arg Arg
1               5                   10

<210> SEQ ID NO 22
<211> LENGTH: 12
<212> TYPE: PRT
<213> ORGANISM: Saccharomyces cerevisiae

<400> SEQUENCE: 22

Met Pro Thr Arg His Asn Val Arg Trp Glu Glu Asn

<210> SEQ ID NO 23
<211> LENGTH: 12
<212> TYPE: PRT
<213> ORGANISM: Saccharomyces cerevisiae

<400> SEQUENCE: 23

Arg Ser Trp Phe Lys Ala Arg Lys Arg Arg Asp Ile
1               5                   10

<210> SEQ ID NO 24
<211> LENGTH: 12
<212> TYPE: PRT
<213> ORGANISM: Saccharomyces cerevisiae

<400> SEQUENCE: 24

Lys Pro Arg Glu Arg His Ile Lys Phe Asn Asp Asn
1               5                   10

<210> SEQ ID NO 25
<211> LENGTH: 11
<212> TYPE: PRT
<213> ORGANISM: Mus musculus

<400> SEQUENCE: 25

Arg Arg Asn Phe Val Asn Lys Leu Lys Pro Leu
1               5                   10

<210> SEQ ID NO 26
<211> LENGTH: 12
<212> TYPE: PRT
<213> ORGANISM: Mus musculus

<400> SEQUENCE: 26

Asn Gln Ala Lys Lys Arg Val Val Phe Ala Asp Ser
1               5                   10

<210> SEQ ID NO 27
<211> LENGTH: 12
<212> TYPE: PRT
<213> ORGANISM: Mus musculus

<400> SEQUENCE: 27

Thr Val Lys Val Lys Asn Val Ser Phe Glu Lys Lys
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 28

Leu Asp Phe Arg Asn Arg Leu Gln Thr Asn
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 29

```
Lys Lys Val Lys Lys Arg Val Ser Phe Ala Asn Asp
1               5                   10

<210> SEQ ID NO 30
<211> LENGTH: 12
<212> TYPE: PRT
<213> ORGANISM: Homo sapiens

<400> SEQUENCE: 30

Arg His Phe Val Asn Lys Leu Lys Pro Leu Lys Ser
1               5                   10

<210> SEQ ID NO 31
<211> LENGTH: 12
<212> TYPE: PRT
<213> ORGANISM: Homo sapiens

<400> SEQUENCE: 31

Asn Gln Ala Lys Lys Arg Val Val Phe Ala Asp Ser
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 32

Thr Cys Phe Arg Pro Arg Leu Arg Gly Ser
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 33

Ser Gln Lys Lys Arg Val Val Phe Ala Asp Met
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 34

Gly Glu Val Phe Ile Asn Lys Gly Lys Gly Phe
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 35

Arg Gly Arg Gln Leu Arg Val Arg Phe Ala Thr His
1               5                   10
```

```
<210> SEQ ID NO 36
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 36

Gln Val Lys Phe Arg Arg Arg Arg Glu Gly
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 37

Tyr Phe Lys Arg Tyr Gln Val Lys Phe Arg Arg Arg
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 38

Glu Asp Phe Lys Ala Lys Lys Lys Glu Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 39

Arg Ile Thr Pro Ser Tyr Val Ala Phe Thr Pro Glu
1               5                   10

<210> SEQ ID NO 40
<211> LENGTH: 13
<212> TYPE: PRT
<213> ORGANISM: Homo sapiens

<400> SEQUENCE: 40

Ser Val Phe Met Gln Arg Leu Lys Thr Asn Ile Leu Gln
1               5                   10

<210> SEQ ID NO 41
<211> LENGTH: 12
<212> TYPE: PRT
<213> ORGANISM: Homo sapiens

<400> SEQUENCE: 41

Ile Asp Glu Val Lys Asn Val Tyr Phe Lys Asn Phe
1               5                   10

<210> SEQ ID NO 42
<211> LENGTH: 12
<212> TYPE: PRT
<213> ORGANISM: Homo sapiens
```

-continued

```
<400> SEQUENCE: 42

Val Leu Lys Val Ser Trp Ile Thr Phe Leu Leu Ala
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 43

Leu Gln Phe Glu Leu Arg Tyr Arg Pro Val
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 44

Thr Thr Lys Ala Val Met Phe Ala Lys
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 45

Asp Leu Phe Glu Asn Arg Lys Lys Lys Asn
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 46

Val Arg Arg Val Phe Ile Met
1               5

<210> SEQ ID NO 47
<211> LENGTH: 9
<212> TYPE: PRT
<213> ORGANISM: Homo sapiens

<400> SEQUENCE: 47

Phe Phe Lys Asn Glu Lys Met Leu Tyr
1               5

<210> SEQ ID NO 48
<211> LENGTH: 12
<212> TYPE: PRT
<213> ORGANISM: Homo sapiens

<400> SEQUENCE: 48

Arg Arg Gly Ser Pro Arg Val Arg Phe Glu Asp Gly
1               5                   10
```

```
<210> SEQ ID NO 49
<211> LENGTH: 11
<212> TYPE: PRT
<213> ORGANISM: Homo sapiens

<400> SEQUENCE: 49

Arg Gln Phe Glu Met Lys Arg Lys Leu His Tyr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 50

Asn Trp Gly Arg Ile Val Ala Phe Phe Ser Phe Gly
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 51

Asn Trp Gly Arg Ile Ala Ala Ala Phe Ser Phe Gly
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 52

Gly Asp Glu Phe Glu Leu Arg Tyr Arg Arg Ala Phe
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 53

Gly Asp Glu Gly Glu Leu Gly Tyr Gly Arg Ala Phe
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 54

Gly Asp Glu Ser Glu Leu Ser Tyr Ser Arg Ala Phe
1               5                   10

<210> SEQ ID NO 55
<211> LENGTH: 12
```

```
<212> TYPE: PRT
<213> ORGANISM: Artificial Sequence
<220> FEATURE:
<223> OTHER INFORMATION: Synthetic Peptide

<400> SEQUENCE: 55

Gly Asp Glu Phe Glu Leu Gly Tyr Gly Arg Ala Phe
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 56

Gly Asp Glu Phe Glu Leu Ser Tyr Ser Arg Ala Phe
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 57

Gly Asp Glu Gly Glu Leu Arg Tyr Arg Arg Ala Phe
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 58

Gly Asp Glu Ser Glu Leu Arg Tyr Arg Arg Ala Phe
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 59

Gly Asp Glu Gly Glu Leu Gly Tyr Arg Arg Ala Phe
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 60

Gly Asp Glu Ser Glu Leu Ser Tyr Arg Arg Ala Phe
1               5                   10

<210> SEQ ID NO 61
<211> LENGTH: 13
<212> TYPE: PRT
```

<213> ORGANISM: Artificial Sequence
<220> FEATURE:
<223> OTHER INFORMATION: Synthetic Peptide

<400> SEQUENCE: 61

Pro Asn Trp Gly Arg Leu Val Ala Phe Phe Val Phe Gly
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 62

Pro Asn Trp Gly Arg Leu Ala Ala Ala Phe Val Phe Gly
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 63

Gly Asp Glu Phe Glu Thr Arg Phe Arg Arg Thr Phe Ser
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 64

Gly Asp Glu Gly Glu Thr Gly Phe Gly Arg Thr Phe Ser
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 65

Gly Asp Glu Phe Glu Thr Gly Phe Gly Arg Thr Phe Ser
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 66

Gly Asp Glu Phe Glu Thr Arg Phe Gly Arg Thr Phe Ser
1               5                   10

<210> SEQ ID NO 67
<211> LENGTH: 13
<212> TYPE: PRT
<213> ORGANISM: Artificial Sequence

```
<220> FEATURE:
<223> OTHER INFORMATION: Synthetic Peptide

<400> SEQUENCE: 67

Gly Asp Glu Gly Glu Thr Gly Phe Arg Arg Thr Phe Ser
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 68

Gly Asp Glu Gly Glu Thr Arg Phe Arg Arg Thr Phe Ser
1               5                   10

<210> SEQ ID NO 69
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 69

Val Lys Gln Ala Leu Arg Glu Ala Gly Asp Phe Glu Leu Arg Tyr Arg
1               5                   10                  15

Arg Ala Phe Ser Asp Thr Ser
            20

<210> SEQ ID NO 70
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 70

Glu Leu Phe Arg Asp Gly Val Asn Trp Gly Arg Ile Val Ala Phe Phe
1               5                   10                  15

Ser Phe Gly Gly Ala Leu
            20

<210> SEQ ID NO 71
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 71

Arg Ala Ala Gly Asp Glu Phe Glu Thr Arg Arg Thr Phe Ser Asp
1               5                   10                  15

Leu Ala Ala Gln Leu His Val
            20

<210> SEQ ID NO 72
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 72
```

```
Glu Leu Phe Gln Gly Gly Pro Asn Trp Gly Arg Leu Val Ala Phe Phe
1               5                   10                  15

Val Gly Ala

<210> SEQ ID NO 73
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 73

His Thr Leu Arg Gln Ala Gly Asp Asp Phe Ser Arg Arg Tyr Arg Arg
1               5                   10                  15

Asp Phe Ala Glu Met Ser Ser Gln
            20

<210> SEQ ID NO 74
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 74

Glu Leu Phe Arg Asp Gly Val Asn Trp Gly Arg Ile Val Ala Phe Phe
1               5                   10                  15

Glu Phe Gly Gly
            20

<210> SEQ ID NO 75
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 75

Phe Arg Gly Arg Ser Arg Ser Ala Pro Pro Asn Leu Trp Ala Ala Gln
1               5                   10                  15

Arg Tyr Gly Arg Glu Leu Arg Arg Met Ser Asp Glu Glu Phe
            20                  25                  30

<210> SEQ ID NO 76
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 76

Phe Arg Gly Arg Ser Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 77

Arg Ser Arg Ser Ser Ala Pro
1               5
```

<210> SEQ ID NO 78
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 78

Glu Glu Glu Leu Ser Phe Arg Gly Arg Ser Arg Ser Ala
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 79

Glu Glu Glu Leu Glu Phe Arg Gly Arg Ser Arg Ser Ala
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 80

Glu Glu Glu Leu Gly Phe Arg Gly Arg Ser Arg Ser Ala
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 81

Arg Gln Ala Gly Asp Asp Phe Ser Arg Arg Tyr Arg
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 82

Arg Gln Ala Gly Asp Asp Phe Glu Arg Arg Tyr Arg
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 83

Arg Gln Ala Gly Asp Asp Phe Gly Arg Arg Tyr Arg
1               5                   10

```
<210> SEQ ID NO 84
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 84

Arg Ser Arg Ser Ser Ala Pro
1               5

<210> SEQ ID NO 85
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 85

Gln Phe Glu Arg Lys Asn Glu Lys Leu Asp
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 86

Leu Ile Arg Ser Lys Ser Val His Phe Asp Gln Ala
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 87

Ser Leu Glu Phe Leu His Lys Pro Arg Arg Leu Ser
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 88

Gln Arg Ser Lys Ser Val His Phe Asp
1               5

<210> SEQ ID NO 89
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 89

Asp Leu Phe Asn Glu Arg Arg Gln Arg Arg
1               5                   10

<210> SEQ ID NO 90
```

```
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 90

Met Pro Thr Arg His Asn Val Arg Trp Glu Glu Asn
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 91

Arg Ser Trp Phe Lys Ala Arg Lys Arg Arg Asp Ile
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 92

Lys Pro Arg Glu Arg His Ile Lys Phe Asn Asp Asn
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 93

Arg Arg Asn Phe Val Asn Lys Leu Lys Pro Leu
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 94

Asn Gln Ala Lys Lys Arg Val Val Phe Ala Asp Ser
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 95

Leu Asp Phe Arg Asn Arg Leu Gln Thr Asn
1               5                   10

<210> SEQ ID NO 96
<211> LENGTH: 12
```

```
<212> TYPE: PRT
<213> ORGANISM: Artificial Sequence
<220> FEATURE:
<223> OTHER INFORMATION: Synthetic Peptide

<400> SEQUENCE: 96

Lys Lys Val Lys Lys Arg Val Ser Phe Ala Asn Asp
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 97

Arg His Phe Val Asn Lys Leu Lys Pro Leu Lys Ser
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 98

Asn Gln Ala Lys Lys Arg Val Val Phe Ala Asp Ser
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 99

Thr Cys Phe Arg Pro Arg Leu Arg Gly Ser
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 100

Ser Gln Lys Lys Lys Arg Val Val Phe Ala Asp Met
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 101

Gly Glu Val Phe Ile Asn Lys Gly Lys Gly Phe
1               5                   10

<210> SEQ ID NO 102
<211> LENGTH: 12
<212> TYPE: PRT
```

```
<213> ORGANISM: Artificial Sequence
<220> FEATURE:
<223> OTHER INFORMATION: Synthetic Peptide

<400> SEQUENCE: 102

Arg Gly Arg Gln Leu Arg Val Arg Phe Ala Thr His
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 103

Gln Val Lys Phe Arg Arg Arg Arg Phe Gly
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 104

Tyr Phe Lys Arg Lys Gln Val Lys Phe Arg Arg Arg
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 105

Glu Asp Phe Lys Ala Lys Lys Lys Glu Leu
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 106

Arg Ile Thr Pro Ser Tyr Val Ala Phe Thr Pro Glu
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 107

Ser Val Phe Met Gln Arg Leu Lys Thr Asn Ile Leu Gln
1               5                   10

<210> SEQ ID NO 108
<211> LENGTH: 12
<212> TYPE: PRT
<213> ORGANISM: Artificial Sequence
```

-continued

<220> FEATURE:
<223> OTHER INFORMATION: Synthetic Peptide

<400> SEQUENCE: 108

Ile Asp Glu Val Lys Asn Val Tyr Phe Lys Asn Phe
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 109

Val Leu Lys Val Ser Trp Ile Thr Phe Leu Leu Ala
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 110

Leu Gln Phe Glu Leu Arg Tyr Arg Pro Val
1               5                   10

<210> SEQ ID NO 111
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 111

Thr Thr Lys Ala Val Met Phe Ala Lys
1               5

<210> SEQ ID NO 112
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 112

Asp Leu Phe Glu Asn Arg Lys Lys Lys Asn
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 113

Val Arg Arg Val Phe Ile Met
1               5

<210> SEQ ID NO 114
<211> LENGTH: 9
<212> TYPE: PRT
<213> ORGANISM: Artificial Sequence
<220> FEATURE:

-continued

```
<223> OTHER INFORMATION: Synthetic Peptide

<400> SEQUENCE: 114

Phe Phe Lys Asn Glu Lys Met Lys Tyr
1               5

<210> SEQ ID NO 115
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 115

Arg Arg Gly Ser Pro Arg Val Arg Phe Glu Asp Gly
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 116

Arg Gln Phe Glu Met Lys Arg Lys Leu His Tyr
1               5                   10
```